United States Patent [19]
Anton et al.

[11] Patent Number: 5,834,262
[45] Date of Patent: *Nov. 10, 1998

[54] OXIDATION OF GLYCOLIC ACID TO GLYOXYLIC ACID USING A MICROBIAL CELL TRANSFORMANT AS CATALYST

[75] Inventors: David Leroy Anton; Robert DiCosimo, both of Wilmington, Del.

[73] Assignee: E. I. du Pont de Nemours and Company, Wilmington, Del.

[ * ] Notice: The term of this patent shall not extend beyond the expiration date of Pat. No. 5,541,094.

[21] Appl. No.: 606,144

[22] Filed: Feb. 23, 1996

Related U.S. Application Data

[63] Continuation-in-part of Ser. No. 256,086, Jun. 30, 1994, which is a continuation-in-part of Ser. No. 817,165, Jan. 6, 1992, abandoned.

[51] Int. Cl.$^6$ .............................. C12P 7/40; C12N 9/04; C12N 15/53
[52] U.S. Cl. ................... 435/136; 435/172.3; 435/190
[58] Field of Search .................... 435/146, 136, 435/172.3, 190, 818

[56] References Cited

U.S. PATENT DOCUMENTS

| | | | |
|---|---|---|---|
| 3,281,460 | 10/1966 | Gandon | 569/531 |
| 4,094,928 | 6/1978 | Gaertner et al. | 558/169 |
| 4,146,731 | 3/1979 | Ogahara et al. | 562/531 |
| 4,233,452 | 11/1980 | Williams et al. | 549/79 |
| 4,235,684 | 11/1980 | Harada et al. | 204/433 |
| 4,455,371 | 6/1984 | Richardson et al. | 435/25 |
| 4,670,191 | 6/1987 | Kleiner et al. | 562/17 |
| 4,851,159 | 7/1989 | Fields et al. | 562/17 |
| 4,855,231 | 8/1989 | Stroman et al. | 435/69.1 |
| 4,871,669 | 10/1989 | Murray et al. | 435/147 |
| 4,935,349 | 6/1990 | McKnight et al. | 435/69.5 |
| 5,219,745 | 6/1993 | Anton et al. | 435/136 |
| 5,221,621 | 6/1993 | Anton et al. | 435/136 |
| 5,541,094 | 7/1996 | Anton et al. | 435/136 |

FOREIGN PATENT DOCUMENTS

| | | |
|---|---|---|
| 0 186 648 | 12/1985 | European Pat. Off. . |
| 0 413 672 | 2/1991 | European Pat. Off. . |
| WO 91/05868 | 5/1991 | WIPO . |

OTHER PUBLICATIONS

Sudbery, P.E. et al, *Biochem. Soc. Trans.*, 16(6), 1081–1083 (1988).
Anand, R. et al, *Trends in Biochemistry*, 10, 413–417 (1992).
Gellissen, G. et al, *Biotech. Adv.*, 10, 179–189 (1992).
Macheroux, P. et al, *Biochimica et Biophysica Acta*, 1132, 11–16 (1992).
Tolbert, N.E. et al, *J. Biol. Chem.*, 181, 905–914 (1949).
Richardson, K.E. et al, *J. Biol Chem.*, 236, 1280–1284 (1961).
Clagett, C.O. et al, *J. Biol. Chem.*, 178, 977–987 (1961).
Zelitch, I. et al., *J. Biol. Chem.*, 201, 707–718 (1953).
Robinson, J.C. et al, *J. Biol. Chem.*, 237, 2001–2010 (1962).
Frigerio, N.A. et al, *J. Biol. Chem.*, 231, 135–157 (1958).
Zelitch, I. et al, *Methods of Enzymology*, 1, Academic Press, New York, pp. 528–532 (1955).
Nishimura, M. et al, *Arch. Biochem. Biophys.*, 222, 397–402 (1983).
Asker, H. et al, *Biochim. Biophys. Acta*, 761, 103–108 (1983).
Emes, M.J. et al, *Int. J. Biochem.*, 16, 1373–1378 (1984).
Cederlund, E. et al, *Eur. J. Biochem.*, 173, 523–530 (1988).
Lindquist, Y. et al, *J. Biol. Chem.*, 264, 3624–3628 (1989).
Yagai, *Methods of Biochemical Analysis*, X, 319–355 (1962).
Volokito et al, *J. Biol. Chem.*, 262, 15825 (1987).
*Ullmans Encyklopadie der technischen Chemie*, 4th Ed., vol. 12, Verlag Chemie, Weinheim, p. 381 (1976).
Macheroux, P. et al, *Biochemistry*, 30, 4612–4619 (1991).
Tanaka, A. et al, *Chemical Abstracts*, 112(13), Abstract No. 113606b, p. 239 (1990),
Takahashi, M., *Chemical Abstracts*, 109(7), Abstract No. 49626s, p. 200 (1988).

*Primary Examiner*—Robert A. Wax
*Assistant Examiner*—Gabriele E. Bugalsky

[57] ABSTRACT

An improved process for preparing glyoxylic acid comprising using the enzyme glycolate oxidase in the form of permeabilized microbial cell transformants selected from *Aspergillus nidulans, Hansenula polymorpha, Pichia pastoris* and *Escherichia coli* to oxidize glycolic acid with oxygen in an aqueous solution that includes an amine.

11 Claims, 11 Drawing Sheets

```
  1 MEITNVNEYE AIAKQKLPKM VYDYYASGAE DQWTLAENRN AFSRILFRPR
 51 ILIDVTNIDM TTTILGFKIS MPIMIAPTAM QKMAHPEGEY ATARAASAAG
101 TIMTLSSWAT SSVEEVASTG PGIRFFQLYV YKDRNVVAQL VRRAERAGFK
151 AIALTVDTPR LGRREADIKN RFVLPPFLTL KNFEGIDLGK MDKANDSGLS
201 SYVAGQIDRS LSWKDVAWLQ TITSLPILVK GVITAEDARL AVQHGAAGII
251 VSNHGARQLD YVPATIMALE EVVKAAQGRI PVFLDGGVRR GTDVFKALAL
301 GAAGVFIGRP VVFSLAAEGE AGVKKVLQMM RDEFELTMAL SGCRSLKEIS
351 RSHIAADWDG PSSRAVARL
```

FIG. 1

OXIDATION OF GLYCOLIC ACID TO GLYOXYLIC ACID USING A MICROBIAL CELL TRANSFORMANT AS CATALYST

This is a continuation-in-part of U.S. Ser. No. 08/256,086 filed Jun. 30, 1994 which is a continuation-in-part of U.S. Ser. No. 07/817,165 filed Jan. 6, 1992 now abandoned.

BACKGROUND OF THE INVENTION

1. Field of the Invention

This invention relates to an improved process for the production of glyoxylic acid by the enzyme catalyzed oxidation of glycolic acid. More specifically, the present invention relates to the use of whole cells of a genetically-engineered microbial transformant, which expresses the enzyme glycolate oxidase [(S)-2-hydroxy-acid oxidase, EC 1.1.3.15], and, optionally, catalase (EC 1.11.1.6).

2. Description of the Related Art

Glycolate oxidase, an enzyme commonly found in leafy green plants and mammalian cells, catalyzes the oxidation of glycolic acid to glyoxylic acid, with the concomitant production of hydrogen peroxide. N. E. Tolbert et al., *J. Biol. Chem.*, Vol. 181, 905–914 (1949) first reported an enzyme, extracted from tobacco leaves, which catalyzed the oxidation of glycolic acid to formic acid and $CO_2$ via the intermediate formation of glyoxylic acid. The addition of certain compounds, such as ethylenediamine, limited the further oxidation of the intermediate glyoxylic acid. The oxidations were carried out at a pH of about 8, typically using glycolic acid concentrations of about 3–40 mM (millimolar). The optimum pH for the glycolate oxidation was reported to be 8.9. Oxalic acid (100 mM) was reported to inhibit the catalytic action of the glycolate oxidase. Similarly, K. E. Richardson and N. E. Tolbert, *J. Biol. Chem.*, vol. 236, 1280–1284 (1961) showed that buffers containing tris(hydroxymethyl)-aminomethane inhibited the formation of oxalic acid in the glycolate oxidase catalyzed oxidation of glycolic acid. C. O. Clagett, N. E. Tolbert and R. H. Burris, *J. Biol. Chem.*, Vol. 178, 977–987 (1949) reported that the optimum pH for the glycolate oxidase catalyzed oxidation of glycolic acid with oxygen was about 7.8–8.6, and the optimum temperature was 35°–40° C.

I. Zelitch and S. Ochoa, *J. Biol. Chem.*, Vol. 201, 707–718 (1953), and J. C. Robinson et al., *J. Biol. Chem.*, Vol. 237, 2001–2009 (1962), reported that the formation of formic acid and $CO_2$ in the spinach glycolate oxidase-catalyzed oxidation of glycolic acid resulted from the nonenzymatic reaction of $H_2O_2$ with glyoxylic acid. They observed that addition of catalase, an enzyme that catalyzes the decomposition of $H_2O_2$, greatly improved the yields of glyoxylic acid by suppressing the formation of formic acid and $CO_2$. The addition of flavin mononucleotide (FMN) was also found to greatly increase the stability of the glycolate oxidase.

N. A. Frigerio and H. A. Harbury, *J. Biol. Chem.*, Vol. 231, 135–157 (1958) have reported on the preparation and properties of glycolic acid oxidase isolated from spinach. The purified enzyme was found to be very unstable in solution; this instability was ascribed to the relatively weak binding of flavin mononucleotide (FMN) to the enzyme active site, and to the dissociation of enzymatically active tetramers and/or octamers of the enzyme to enzymatically-inactive monomers and dimers, which irreversibly aggregate and precipitate. The addition of flavin mononucleotide (FMN) to solutions of the enzyme greatly increased its stability, and high protein concentrations or high ionic strength maintained the enzyme as octamers or tetramers.

There are numerous other references to the oxidation of glycolic acid catalyzed by glycolic acid oxidase, for example:

Isolation of the enzyme (usually includes an assay method):

I. Zelitch in *Methods of Enzymology*, Vol. 1, Academic Press, New York, 1955, p. 528–532, from spinach and tobacco leaves.

M. Nishimura et al., *Arch. Biochem. Biophys.*, Vol. 222, 397–402 (1983), from pumpkin cotyledons.

H. Asker and D. Davies, *Biochim. Biophys. Acta*, Vol. 761, 103–108 (1983), from rat liver.

M. J. Emes and K. H. Erismann, *Int. J. Biochem.*, Vol. 16, 1373–1378 (1984), from Lemna Minor L.—Structure of the enzyme:

E. Cederlund et al., *Eur. J. Biochem.*, Vol. 173, 523–530 (1988).

Y. Lindquist and C. Branden, *J. Biol. Chem.* Vol. 264, 3624–3628, (1989).

SUMMARY OF THE INVENTION

This invention relates to a process for the production of glyoxylic acid (OCHCOOH), where glycolic acid ($HOCH_2COOH$) (200 to about 2500 mM) and oxygen are reacted in an aqueous solution (pH 7 to 10) in the presence of whole cells of a genetically-engineered microbial transformant, which expresses the enzyme glycolate oxidase [(S)-2-hydroxy-acid oxidase, EC 1.1.3.15], and, optionally, catalase (EC 1.11.1.6). Under optimum conditions, very high yields of glyoxylic acid are obtained at high conversion of glycolic acid, and the genetically-engineered microbial transformant can be recovered and reused.

BRIEF DESCRIPTION OF THE DRAWINGS

FIG. 1 illustrates the amino acid sequence of spinach glycolate oxidase (SEQ. ID NO.; 1).

DETAILED DESCRIPTION OF THE INVENTION

Figure 2:
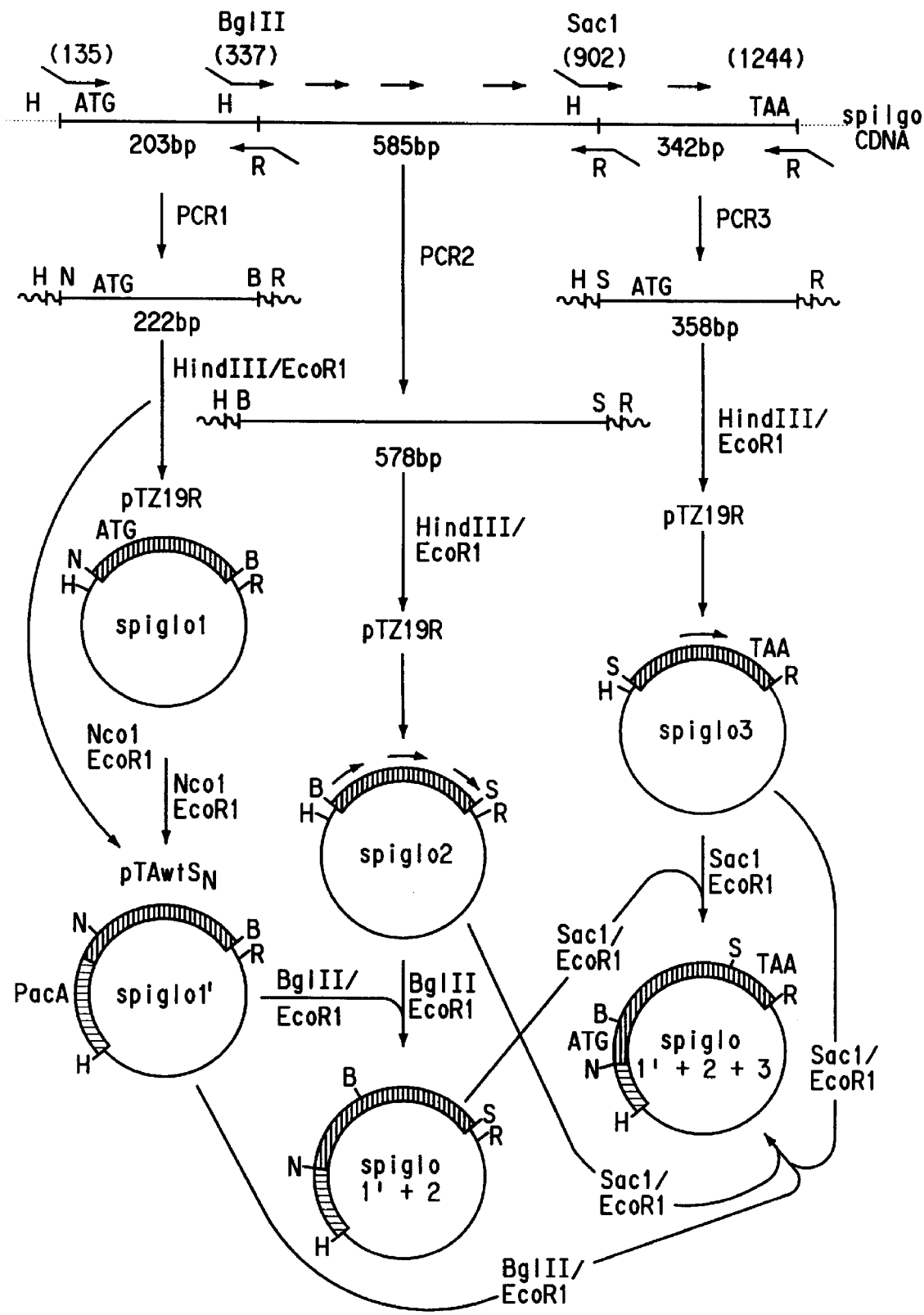
FIG. 2 illustrates the steps taken to amplify glycolate oxidase-encoding cDNA by polymerase chain reaction.

This invention describes the use of whole cells of a microbial transformant (e.g., *Aspergillus nidulans, Pichia*

*pastoris, Hansenula polymorpha* and *Escherichia coli*) which co-expresses glycolate oxidase and catalase for the manufacture of glyoxylic acid from glycolic acid (hydroxyacetic acid). Although the enzyme-catalyzed reaction of glycolic acid with oxygen has been known for many years, high selectivities (>99%) to glyoxylic acid have not been previously obtained, nor has the oxidation of glycolic acid been performed at concentrations of 0.20M to 2.5M. A previous, commonly assigned patent, U.S. Pat. No. 5,219, 745 (Jun. 15, 1993), "Production of Glyoxylic Acid from Glycolic Acid", described a process for the enzymatic conversion of glycolic acid to glyoxylic acid in the presence of oxygen, an amine buffer, and the soluble enzymes glycolate oxidase and catalase. This process demonstrated the unexpected synergistic effect of using both catalase (to destroy by-product hydrogen peroxide) and an amine buffer capable of forming a chemical adduct with the glyoxylic acid produced (limiting its further oxidation) and is herein incorporated by reference for such purpose. Neither the separate addition of catalase or an amine buffer were found to produce the high selectivity observed when both were present, and the almost quantitative yields of glyoxylic acid obtained were more than expected from a simple additive effect of using catalase or amine buffer alone. The instant invention is viewed as an improvement to the above process in that the present invention uses a whole microbial cell as a catalyst, in place of the soluble enzymes.

The previously-reported use of soluble enzymes as catalysts poses several problems: catalyst recovery for reuse is not easily performed, catalyst stability is not as good as can be obtained with immobilized enzyme or whole cell microbial catalysts, and soluble enzymes are not stable to the sparging of the reaction mixture with oxygen (required to increase the rate of oxygen dissolution and, thus, reaction rate). Several transformants of *Aspergillus nidulans, Pichia pastoris, Hansenula polymorpha* and *Escherichia coli* have now been constructed, using genetic engineering techniques commonly known to those skilled in the art, which express the glycolate oxidase from spinach as well as an endogenous catalase. Several advantages are offered by the use of these whole cell catalysts in the previously described process: 1) the whole cell catalysts are easily recovered from the reaction mixture at the conclusion of the reaction for reuse, whereas the soluble enzyme is only recovered with great difficulty and loss of activity, 2) the whole cell catalysts are more stable than the soluble enzyme, both for the number of catalyst turnovers obtained versus the soluble enzyme, as well as for recovered enzyme activity at the conclusion of a reaction, and 3) most importantly, the whole cell catalyst is stable to reaction conditions where oxygen is sparged into the reaction mixture to increase the rate of oxygen dissolution and reaction rate, where under similar reaction conditions the soluble glycolate oxidase is rapidly denatured.

The transformants are required to be permeable to the passage of carboxylic acids under the reaction conditions described herein; transformants of *Escherichia coli* and *Aspergillus nidulans* become permeabilized when used as catalysts in the present process, while transformants of *Hansenula polymorpha* and *Pichia pastoris* require permeabilization prior to use as catalysts in the present process (described hereinafter). It was discovered that these permeabilized transformant catalysts were stable to the reaction conditions of the present process; that is, the integrity of the cell was maintained under the present reaction conditions which include high sparge rates, high shear forces generated by rapid stirring, and high concentrations of glycolic or glyoxylic acids and organic amines. It is critical to the successful operation of this process that the transformant cells do not lyse (do not break apart) and release the contents of the cells (including the glycolate oxidase and catalase enzymes) into the reaction mixture, where rapid loss of glycolate oxidase enzymatic activity would occur.

The glycolate oxidase expressed in a microbial transformant may have a structure corresponding to any naturally occurring form of the enzyme, or may have a genetically engineered variant structure, provided however that enzymatically-active glycolate oxidase, as defined above, is retained. Naturally occurring forms of glycolate oxidase include, for example, spinach-produced glycolate oxidase. As shown in FIG. 1 herein, spinach glycolate oxidase consists, in its mature form, of 369 amino acids arranged in the indicated sequence (SEQ. ID NO.: 1). According to a preferred embodiment of the present invention, the glycolate oxidase is spinach glycolate oxidase or an enzymatically-active variant of spinach glycolate oxidase, e.g., a enzymatically-active fragment of the enzyme, or an analogue in which one or more amino acids is replaced using conservative amino acid replacements, or a variant in which the region of the enzyme which directs its peroxisomal accumulation is deleted (see Macheroux et al., *Biochem.*, vol. 30, 4612 (1991), incorporated herein by reference).

The *Aspergillus nidulans* transformants were prepared by first cloning the spinach gene which codes for glycolate oxidase and then introducing this gene into a strain of *Aspergillus nidulans* which already produced acceptable levels of the endogenous catalase. A variety of genetic constructs, adapted to receive heterologous DNA and to control expression thereof, have been developed for use with Aspergillus hosts and any of these may be employed for the purpose of producing glycolate oxidase in the Aspergillus host. Such genetic constructs, conventionally referred to as expression cassettes, comprise a region 5' of the heterologous DNA insert which harbours transcriptional and translational initiation controls, and a region 3' of the DNA insert which controls translational termination and, optionally, transcriptional termination. Both control regions are derived typically from genes homologous to Aspergillus, although it is to be understood that such control regions need not be derived from the genes native to the specific species chosen as glycolate oxidase production host, and need not be derived from the same Aspergillus gene.

Initiation control regions, more commonly referred to as promoters, which are useful to drive expression of glycolate oxidase-encoding DNA include those derived from genes in the ethanol utilization pathway of *Aspergillus nidulans,* including the alcohol dehydrogenase genes alcA, aldA and ADH3 gene. Suitable initiation controls also include those derived from the triose phosphate isomerase genes of *Aspergillus niger* and *Aspergillus nidulans,* the trpc gene of *Aspergillus nidulans,* the amds gene of *Aspergillus nidulans,* the pectin lyase gene of various Aspergillus species as well as the glucoamylase gene of *Aspergillus niger,* and certain amylase genes of *Aspergillus oryzae.*

Termination control regions, which include a polyadenylation site for translational termination and regions functional to terminate transcription, may also be derived from various genes native to Aspergillus hosts, or optionally other filamentous fungal hosts. Such regions may be derived, for example, from the *Aspergillus niger* glucoamylase gene, the *Aspergillus nidulans* trpC gene and the *Mucor miehei* genes. It has been found that transcriptional termination regions are dispensible, but these may be included if desired. Moreover, an Aspergillus-derived polyadenylation site can be unnecessary, provided that the polyadenylation site native to the chosen glycolate oxidase-encoding DNA is incorporated within the expression cassette.

For intracellular production of glycolate oxidase, DNA coding therefore is linked operably, and through its initiation codon, methionine, to the selected expression control region, such that expression results in the formation of glycolate oxidase-encoding messenger RNA. Alternatively, if production of a glycolate oxidase fusion protein is desired, DNA coding for glycolate oxidase is linked at its 5' end, and via the initiating methionine codon, to the 3' end of the gene encoding the carrier protein. Also, if desired, DNA coding for an enzyme-cleavable linker is incorporated without reading frame disruption, between the oxidase-encoding DNA and the carrier-encoding DNA, so that expression yields a fusion protein from which glycolate oxidase can be liberated by enzyme cleavage. A suitable carrier protein is Aspergillus glucoamylase, and suitable cleavable peptide linkers are those cleavable by ubiquitin hydrolase, kex, factor Xa and the like. An example of the fusion protein approach to protein production is provided by Contreras et al., *Bio/Technology,* vol. 9, 378 (1991).

A genetically-engineered microbial transformant *Aspergillus nidulans* T17, harboring multiple copies of the spinach glycolate oxidase-encoding DNA under expression control of the *A. nidulans* alcA promoter, and multiple copies of the *A. nidulans* alkR gene, the product of which regulates function of the alcA promoter, was deposited under the terms of the Budapest Treaty with the Northern Regional Research Center, Peoria, Ill., U.S.A. on Sep. 24, 1992, under NRRL No. 21000. The resulting transformants were cultured in various media (minimal or SYG rich media) in shaker flasks or fermenters, and additionally, different agents such as oleic acid (OL), hydroxyacetic acid (HA), or corn steep liquor (CSL) were added to the media to increase levels of expression of glycolate oxidase and/or catalase. The different transformants were then screened by assaying the *Aspergillus nidulans* whole cells (untreated) for catalase and glycolate oxidase activity, and by running reactions with the cells as catalysts for the oxidation of glycolic acid to glyoxylic acid. When used as catalysts for the oxidation of glycolic acid to glyoxylic acid, the whole cells were not pre-treated or permeabilized to increase accessibility of the reaction mixture to the enzymes in the interior of the cells; some permeabilization of the cells may take place, either from exposure to the reaction mixture or any of its components, or by freezing and thawing, which was used to store the whole cell catalysts until needed.

Many of the deficiencies of the soluble enzymes were eliminated by employing whole cells of *A. nidulans* as catalyst. Recovery and reuse of the whole-cell catalyst was easily performed by centrifugation or by filtering the catalyst away from the reaction mixture and recycling it to fresh reaction mixture; in this manner, turnover numbers for glycolate oxidase of as high as $10^6$ have been obtained. The ability to bubble oxygen through the reaction mixture without denaturing the enzyme catalyst (as is observed when using the soluble enzyme) resulted in increases in the reaction rate of at least ten-fold over reactions where the reaction mixture is not bubbled, and this increase in rate significantly reduces the cost of manufacture for this process.

Several additional microbial transformants which express glycolate oxidase activity as well as endogenous catalase activity have been prepared, and their use as a microbial catalyst in the present invention demonstrated. A second microbial cell catalyst which has been utilized in the present invention is a transformant of *Hansenula polymorpha* (a methylotrophic yeast). The methylotrophic yeast *Hansenula polymorpha* has been developed as an expression system for heterologous proteins (Roggenkamp et al., *Mol. Gen. Genetics,* vol. 202, 302 (1986); Hollenberg and Janowicz, EPA No. 0299108 (1987)). As a facultative methylotroph this yeast species is able to use methanol as sole energy and carbon source; other possible carbon sources are glucose or glycerol. Upon addition of methanol into culture media, key enzymes of the methanol metabolism are strongly expressed. The expression is regulated at a transcriptional level. The genes for these key enzymes dihydroxyacetone synthase (DHAS), formate dehydrogenase (FMD; i.e., FMDH) and methanol oxidase (MOX) have been cloned and characterized (Ledeboer et al., *Nucleic Acids Res.,* vol. 13, 3060 (1985); Janowicz et al., *Nucleic Acids Res.,* vol. 13, 2043 (1985); Hollenberg and Janowicz, 1987). The promoters of these key enzymes are repressed using glucose, derepressed using glycerol and induced using methanol as carbon source.

The promoter elements of these genes can be used for heterologous gene expression. Accordingly, they are components of expression vectors for the generation of recombinant *Hansenula polymorpha* strains. A standard expression vector harbors the coding sequence of a foreign gene integrated between the promoter, for example but not by way of limitation, an FMD-promoter, a MOX-promoter or the like, and generally any terminator, again by way of example but not by way of limitation, a MOX-terminator sequence or the like. In addition, the vectors contain selection markers and a HARS1 (Hansenula autonomously replicating sequence) for selection and propagation in suitable *H. polymorpha* hosts and a bacterial origin of replication (ori) and an ampicillin-resistance (amp) gene for propagation and selection in *E. coli* (Gellissen et al., *Biotech Adv.,* vol. 10, 179 (1992); Gellissen et al., *Tibtech,* vol. 10, 413 (1992)).

After uptake the heterologous DNA is stably integrated into the host's genome. Transformations result in a variety of strains harboring a varying copy number of the integrated DNA in a head-to-tail arrangement. This stable multimeric integration of expression cassettes makes *Hansenula polymorpha* an ideal host for the co-expression of several proteins in a fixed ratio (Janowicz et al., *Yeast,* vol. 7, 431 (1991)).

The construction of an expression cassette for the expression of glycolate oxidase or catalase in Hansenula may be accomplished by means well known to those skilled in the art. The source of the glycolate oxidase gene (or the catalase gene) may either be chromosomal DNA or a previously constructed vector containing the gene. Generally it is most preferred to isolate the glycolate oxidase gene from an already existing vector. It is also preferred that the glycolate oxidase gene be bounded on both the 5' and 3' ends by convenient restrictions sites. Any vector or plasmid containing a suitable glycolate oxidase gene may be used, however, for the purpose of the present invention the plasmid pDA-PCR#1 is most preferred. pDA-PCR#1 is derived from the Aspergillus transformation plasmid pTAwtS-GOD. More specifically, pTAwtS-GOD contains a spinach glycolate oxidase gene under the control of an *Aspergillus nidulans* alcA promoter and bounded at the 5' end by a BglII site and at the 3' end by an EcoRI site. The glycolate oxidase gene in pTAwtS-GOD is amplified by conventional PCR protocols using primers which incorporated an XbaI site at one end and an EcoRI site at the opposite end. The PCR fragment is ligated between the XbaI and EcoRI sites in the Bluescript plasmid (Stratagene, La Jolla, Calif.) to give the plasmid pDA-PCR#1.

Figure 4:
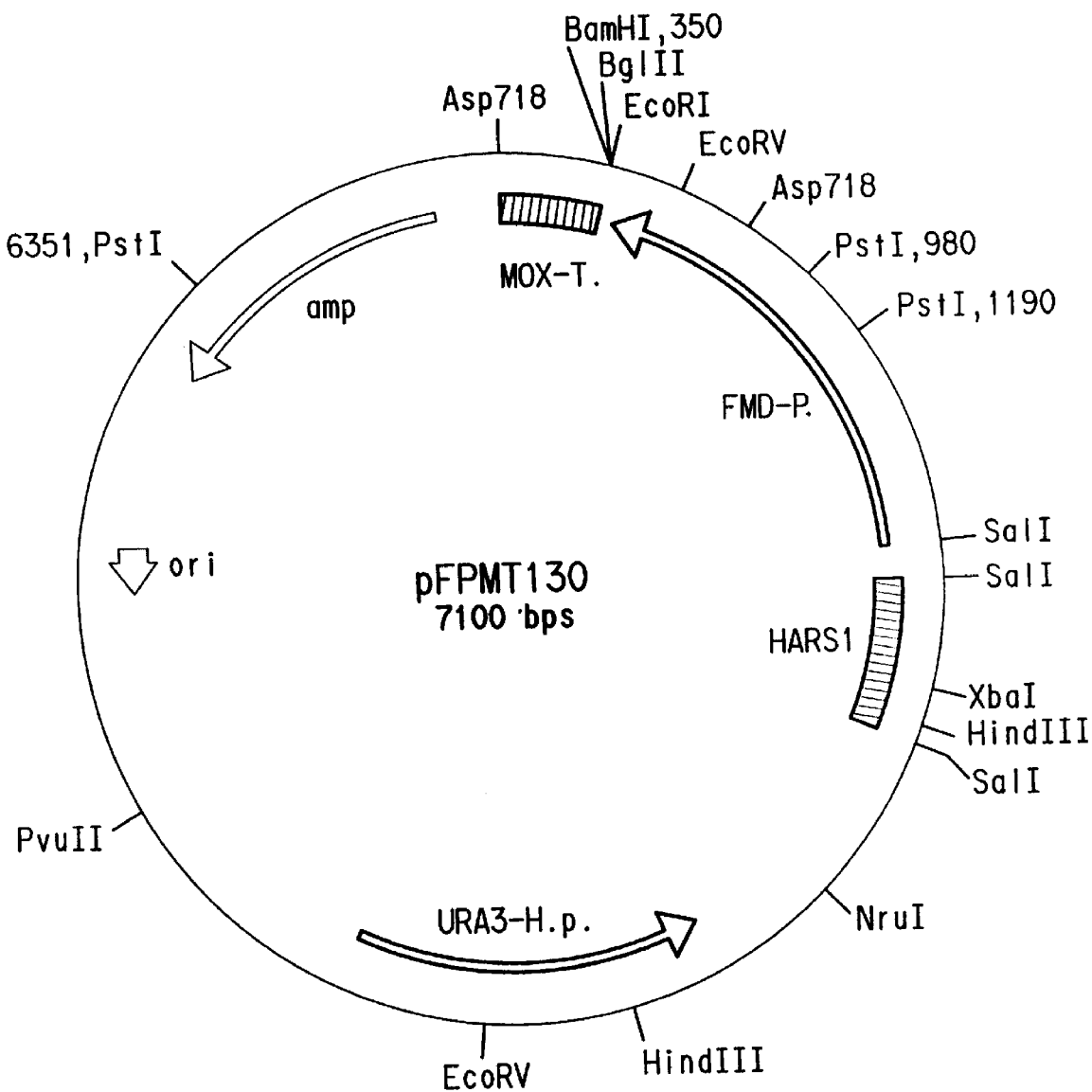
FIG. 4 illustrates the plasmid pFPMT130 expression vector indicating the respective components and restriction sites.
Figure 5:
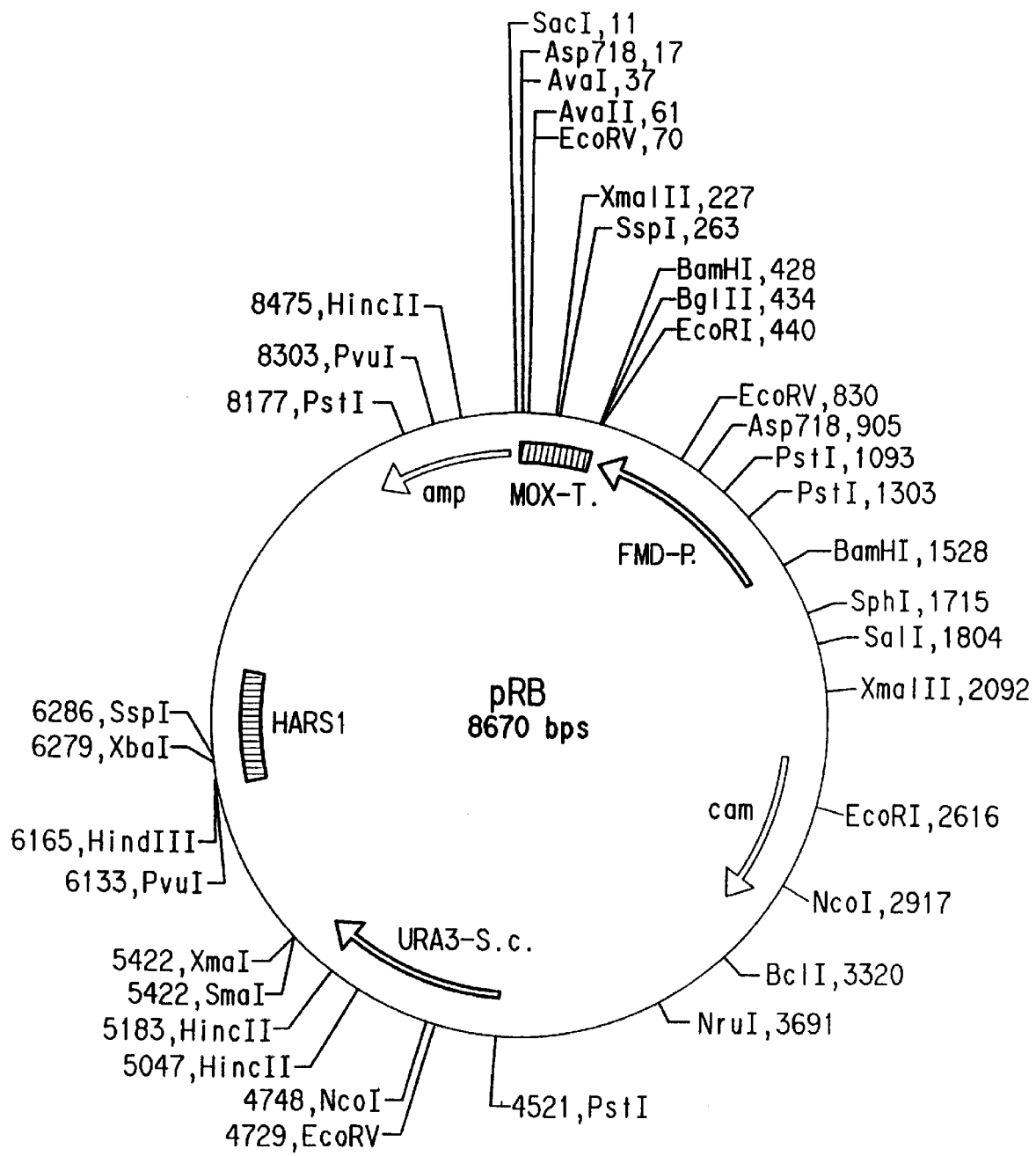
FIG. 5 illustrates the plasmid pRB expression vector indicating the respective components and restriction sites.
Figure 6:
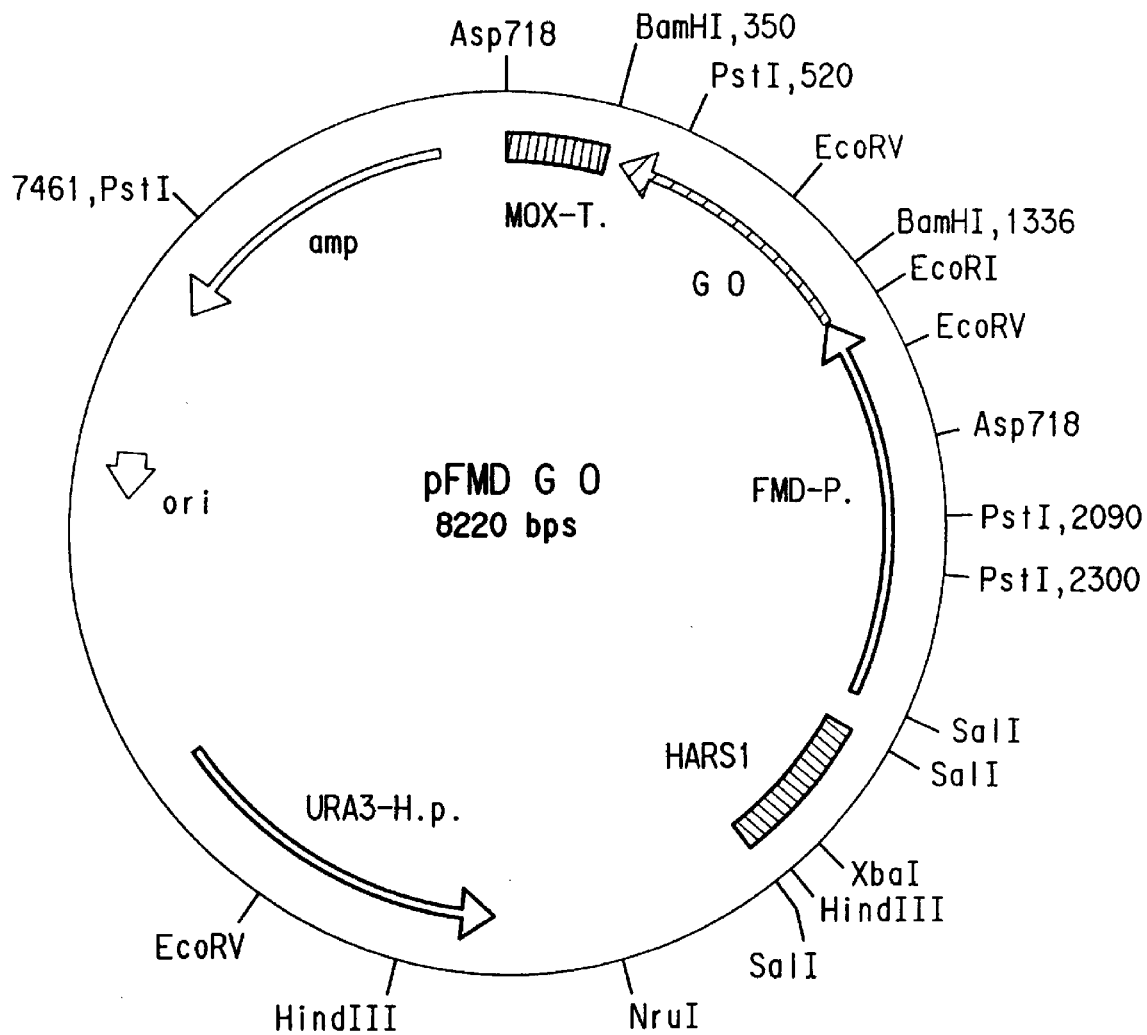
FIG. 6 illustrates the plasmid PFMDGO expression vector indicating the respective components and restriction sites.
Figure 7:
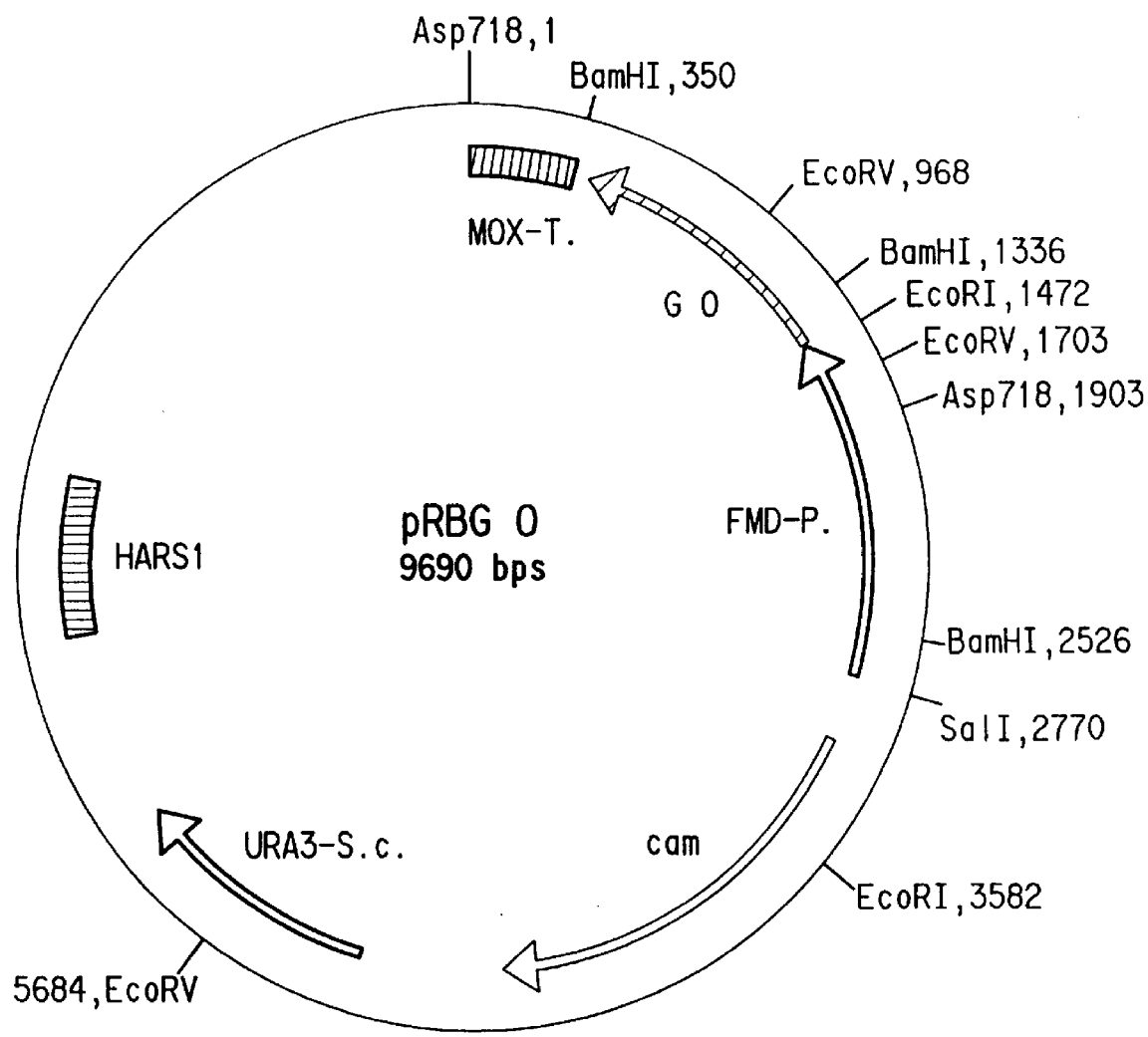
FIG. 7 illustrates the plasmid pRBGO expression vector indicating the respective components and restriction sites.

Isolated DNA encoding the glycolate oxidase protein is optionally amplified by techniques well known in the art for the purpose of cloning into a suitable Hansenula transformation vector. Any method of amplification may be used including Polymerase Chain Reaction (PCR) or Ligase Chain Reaction (LCR) where PCR is most preferred. Amplified glycolate oxidase DNA is then cloned into a suitable Hansenula transformation vector. A number of transformation vectors are suitable where the vector contains a promoter capable of driving the glycolate oxidase gene and where the promoter contains, downstream, a restriction site compatible with the restriction sites flanking the glycolate oxidase gene. Any suitable transformation vector may be used, including pFPMT130 or pRB described in detail in FIGS. 4 and 5. The restricted fragment is cloned into the multiple cloning site of the basic vector pFPMT130 (see FIG. 4) using the EcoRI and the BamHI site for insertion. A second series is constructed in the pRB vector harboring a chloramphenicol resistance sequence as a selection marker (FIG. 5). Restriction, ligation, propagation, and isolation of the newly generated plasmid DNA follows standard procedures as described by Maniatis et al., 1982, Molecular Cloning: a laboratory manual, Cold Spring Harbour Laboratory Press. The insertion of the cDNA sequence results in the expression vectors PFMDGO and pRBGO (FIGS. 6 and 7).

The vectors described above are used to transform competent *H. polymorpha* cells of strain RB11, deficient in orotidine 5' phosphate dehydrogenase (ura⁻). The auxotrophic strain RB11 is generated basically as described by Roggenkamp et al., 1986. Competent cells of this strain are generated according to established protocols (Dohmen et al., Yeast, 7, 691, (1991)) as follows: 10 mL yeast medium (YPD; i.e., yeast, peptone, and glucose) are inoculated with cells and cultured at 37° C. overnight. This culture is subsequently used to inoculate 200 mL of YPD. Cell are cultured at 37° C. until the $OD_{600}$ is between 0.6 and 1.0. Cells are harvested by centrifugation, washed at room temperature with 100 mL of a solution A (1M sorbitol, 10 mM bicine pH 8.35, 3% ethylene glycol) and then resuspended in 4 mL of this solution A; 11 L of dimethylsulfoxide (DMSO) is added and the competent cells are stored at −70° C.

For transformation, 10 g of plasmid DNA and 100 l of cold 0.1M $CaCl_2$ are added to the frozen cell aliquots; after fast thawing 1.0 mL of a solution B (40% PEG 3350, 200 mM bicine pH 8.35) is added, and the transformation mixtures are incubated at 37° C. for 1 hour. Subsequently, cells are washed in 1 mL of a solution C (150 mM NaCl, 10 mM bicine pH 8.35) and resuspended in 200 mL. This suspension is plated on selective agar plates (yeast nitrogen base (YNB)-glucose). Plates are incubated at 37° C. for 3 to 5 days.

Generation of mitotically stable strains with multimeric copies of the heterologous DNA is performed in the following manner. Colonies from developed plates are used to inoculate 3 mL of YNB glucose and cultured at 37° C. A 50 L aliquot of the fully grown culture is used to inoculate another 3 mL culture. This procedure is repeated for some 40 generations of growth. During this passaging plasmid DNA is integrated into the genome. Subsequently 3 mL of YPD (non-selective medium) is inoculated and cultured at 37° C. Plating of a diluted aliquot should result in an identical number of colonies when plated on selective and non-selective agar plates.

Identification of recombinant strains expressing glycolate oxidase (GO) is performed in the following manner. For expression of the recombinant GO the cells have to be cultured under derepressive or inductive conditions. The passaged transformants were used to inoculate 3 mL of YNB supplemented with 1% glycerol. After two days of growth the cells were transferred to 3 mL YNB supplemented with 1% methanol. After a further day of induction cells were harvested by centrifugation (5 min 800× g) and GO activity was determined in samples prepared from crude extracts. Preparation of crude extract is performed by resuspension of harvested cells in 600 mL of extraction buffer (1 mM dithiothreitol (DTT), 0.1 mM flavin mononucleotide (FMN), 10 mM phenol methylsulfonyl fluoride (PMSF), 10% DMSO in 0.1M sodium phosphate buffer pH 8.3). Cells are broken with glass beads (0.45–0.5 mm diameter) for 5 minutes, cooling with solid $CO_2$ every 30 seconds. Cell debris is removed by centrifugation (15 minutes at 15000× g at 4° C.). 5–20 mL of the crude extracts were analyzed for GO content by quantifying the generation of glyoxylic acid by spectrophotometric assay modified after Soda et al., 1973, Agr. Biol. Chem., 37(6):1393.

The copy number of the integrated heterologous DNA in GO-expressing strains is determined as outlined by Gellissen et al., 1992. For DNA determination, DNA is isolated from various transformants and from the untransformed host strain RB11. The isolated DNA is restricted with Asp718/SalI, transferred to nitrocellulose and hybridized to a $^{32}P$-labeled EcoRI/Asp718 fragment. This results in two signals in similar electrophoretic positions for the genuine single copy FMD/GO gene fusion and the heterologous FMD promoter/GO gene fusion. In DNA dilutions the copy number is estimated comparing the signal intensity of the heterologous fragments with that of the intrinsic single copy control.

Transformed strains were passaged and analyzed for GO content as described below. The screening results reported in the Examples were obtained using PFMDGO and pRBGO for transformation. Glycolate oxidase protein may be detected by Western blot analysis or glycolate oxidase activity may be detected by means of a spectrophotometric assay. Most preferred is the method described by Soda, et al., *Agr. Biol. Chem.*, vol. 37, 1393 (1973), herein incorporated by reference. This assay measures the glyoxylate produced by the glycolate oxidase-catalyzed oxidation of glycolate by reacting said glyoxylate with glycine and o-aminobenzaldehyde to form a yellow complex having an absorbance maximum at 440 nm. A genetically-engineered transformant of *Hansenula polymorpha* which produces high levels of glycolate oxidase was selected and designated *H. polymorpha* GO1, and was deposited under the terms of the Budapest Treaty with the Northern Regional Research Center, Peoria, Ill., U.S.A. on Mar. 30, 1993, under NRRL No. Y-21065.

The Hansenula strains were also evaluated for their ability to produce endogenous catalase. For the evaluation of catalase production, transformed *Hansenula polymorpha* was grown according to the procedure described above and analyzed for enzymatically active catalase (i.e., any disproportionation of hydrogen peroxide as determined by assays of conventional design). Several methods of determining catalase activity are available, such as the method of Beers et al., *J. Biol. Chem.*, vol. 195, 133 (1952).

*H. polymorpha* cell catalysts were typically prepared by first growing an inoculum of an *H. polymorpha* transformant in 500 mL of YPD (Difco), pH 4.4. This culture was then inoculated into a fermenter containing 10 L of Yeast Nitrogen Base (YNB, Difco) without amino acids (14 g), ammonium sulfate (50 g) and methanol (100 g), at pH 5.0. The fermenter was operated for 42.5 h at 37° C., an agitation rate of 400 rpm, constant pH of 5.0, 40% dissolved oxygen (controlled), and 14 psig of air. At the conclusion of the fermentation, 1.0 kg of glycerol was added and the cells harvested by centrifugation, frozen in liquid nitrogen, and stored at −80° C.

A third microbial cell catalyst which has been utilized in the present invention is a transformant of *Pichia pastoris* (a methylotrophic yeast) which expresses the glycolate oxidase enzyme from spinach, as well as an endogenous catalase. One class of useful Pichia hosts are auxotrophic mutants, i.e., mutant strains which require supplementation with one or more amino acids, vitamins or other nutrients in order to grow. Transformation of such mutants can be readily selected by employing, as part of the recombinant DNA material used to transform the mutant host, DNA sequences which code for the production of the missing gene product. Most preferred is the host yeast strain mutant *Pichia pastoris* GTS115 (his4), which is a mutant defective in the ability to produce histidine, and has been identified as having the mutant genotype his4. *Pichia pastoris* GTS115 (his4), has been deposited with the Northern Regional Research Laboratories, (NRRL) under the terms of the Budapest Treaty and will be hereinafter referred to by its NRRL accession number NRRL Y-15851. It is of course recognized by those of skill in the art that mutants in many other genes important in Pichia metabolism also exist or can be isolated and therefore virtually any other auxotrophic Pichia host would be suitable for the purpose of the present invention.

A variety of genetic constructs, adapted to receive heterologous DNA and to control expression thereof, have been developed for use with Pichia hosts and any of these may be employed for the purpose of producing glycolate oxidase in the Pichia host. Such genetic constructs, conventionally referred to as expression cassettes, comprise a region 5' of the heterologous DNA insert which harbors transcriptional initiation controls, and a region 3' of the DNA insert which controls transcriptional termination. It is most preferred when both control regions are derived from genes homologous to Pichia although it is to be understood that such control regions need not be derived from the genes native to the specific species chosen as glycolate oxidase production host, and need not be derived from the same Pichia gene.

Initiation control regions, more commonly referred to as promoters, which are useful to drive expression of glycolate oxidase-encoding DNA include those derived from genes in the methanol utilization pathway of Pichia. Virtually any Pichia promoter capable of driving the spinach glycolate oxidase gene is suitable for the present invention including glyceraldyhyde-3-phosphate dehydrogenase and dihydroxy acetone synthase however the most preferred are the alcohol oxidase genes, AOX1.

Termination control regions, which may include a polyadenylation site and regions functional to terminate transcription, may also be derived from various genes native to Pichia hosts, or optionally other yeast hosts or even from spinach. Optionally a Pichia polyadenylation termination site may be unnecessary, however, it is most preferred if they are included.

For intracellular production of glycolate oxidase, DNA encoding glycolate oxidase is linked operably through its initiation codon to the selected expression control region, such that expression results in the formation of glycolate oxidase-encoding messenger RNA. Alternatively, if production of a glycolate oxidase fusion protein is desired, DNA encoding for glycolate oxidase is linked at its 5' end to the 3' end of the gene encoding the carrier protein. Optionally the reverse orientation could be constructed where DNA encoding the carrier protein is linked at its 5' end to the 3' end of the DNA encoding glycolate oxidase. Also, if desired, DNA coding for an enzyme cleavable linker is incorporated without reading frame disruption, between the oxidase-encoding DNA and the carrier-encoding DNA, so that expression yields a fusion protein from which glycolate oxidase can be liberated by enzyme cleavage. An example of the fusion protein approach to protein production is provided by Contreras et al., *Bio/Technology*, vol. 9, 378 (1991).

Figure 8:
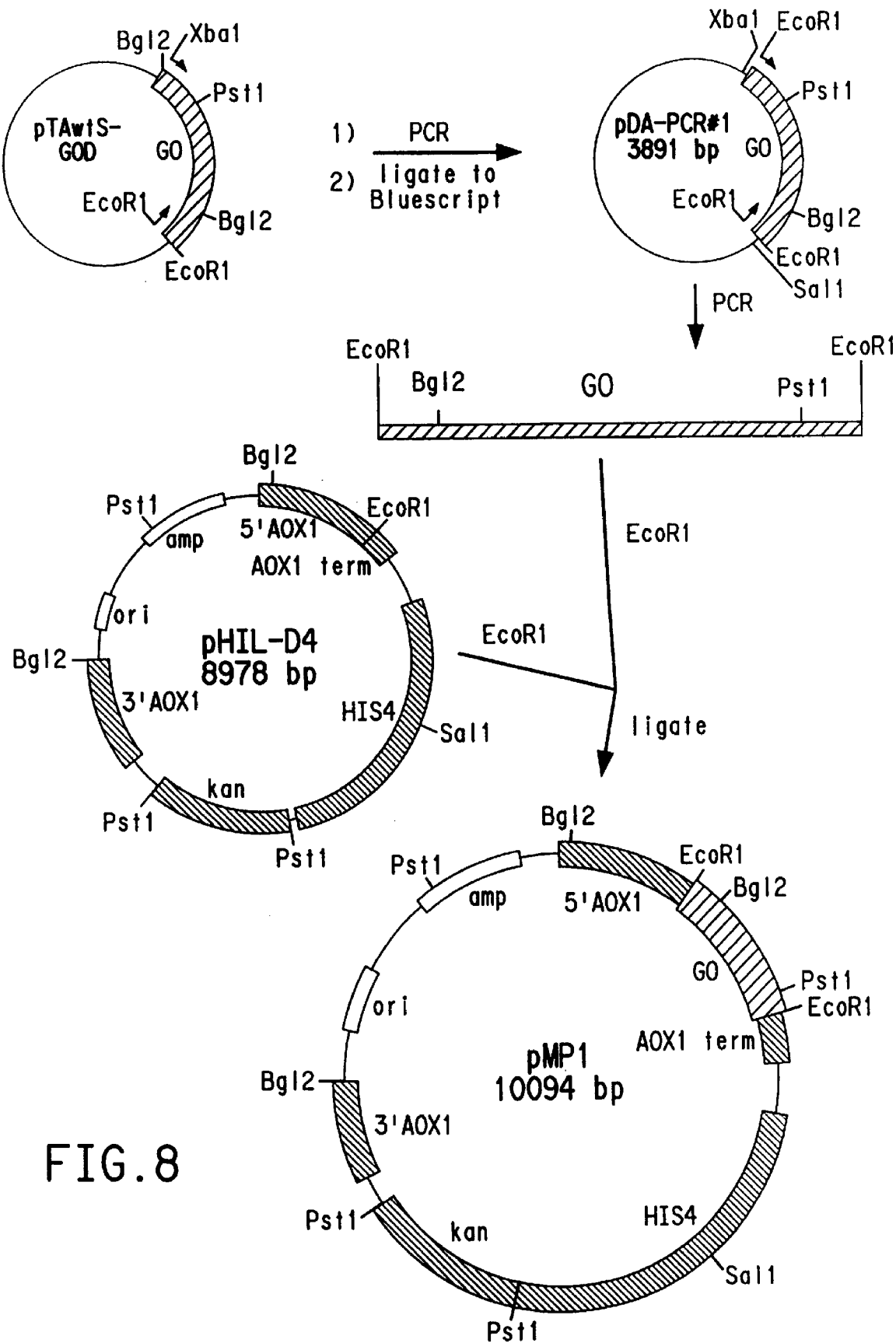
FIG. 8 illustrates the creation of plasmid pMP1 from plasmids pHIL-D4 and pDA-PCR#1.

The construction of an expression cassette for the expression of glycolate oxidase in Pichia may be accomplished by means well known to those skilled in the art. The source of the glycolate oxidase gene may either be chromosomal DNA or a previously constructed vector containing the gene. Generally it is most preferred to isolate the glycolate oxidase gene from an already existing vector. It is also preferred that the glycolate oxidase gene be bounded on both the 5' and 3' ends by convenient restrictions sites. Any vector or plasmid containing a suitable glycolate oxidase gene may be used, however, for the purpose of the present invention the plasmid pDA-PCR#1 is most preferred. pDA-PCR#1 is derived from the Aspergillus transformation plasmid pTAwtS-GOD which is fully described in U.S. Ser. No. 07/817,170, herein incorporated by reference. Briefly, pTAwtS-GOD contains a spinach glycolate oxidase gene under the control of a *Aspergillus nidulans* alcA promoter and bounded at the 5' end by a BglII site and at the 3' end by an EcoRI site, (FIG. 8). The glycolate oxidase gene in pTAwtS-GOD was amplified by conventional PCR protocols using primers which incorporated an XbaI site at one end and an EcoRI site at the opposite end. The PCR fragment was ligated between the XbaI and EcoRI sites in the Bluescript plasmid (Stratagene, La Jolla, Calif.) to give the plasmid pDA-PCR#1.

Isolated DNA encoding the glycolate oxidase protein is optionally amplified by techniques well known in the art for the purpose of cloning into a suitable Pichia transformation vector. Any method of amplification may be used including Polymerase Chain Reaction (PCR) or Ligase Chain Reaction (LCR) where PCR is most preferred. Amplified glycolate oxidase DNA is then cloned into a suitable Pichia transformation vector. A number of transformation vectors are suitable where the vector contains a promoter capable of driving the glycolate oxidase gene and where the promoter contains, downstream, a restriction site compatible with the restriction sites flanking the glycolate oxidase gene. Any suitable transformation vector may be used, including pHIL-A1, pHIL-D1, pHIL-D2, pHIL-D3, pHIL-D5, pHIL-S1, pRK20, and pT76H4, however plasmid pHIL-D4 is most preferred. pHIL-D4 is commercially available from Phillips Corp. (Phillips Petroleum Company, Bartlesville, Okla.) and is described in detail in FIG. 6. Briefly, pHIL-D4 includes the following features (i) *Pichia pastoris* methanol inducible promoter AOX1 linked through an EcoRI site to (ii) AOX1 transcriptional termination element, (iii) a *P. pastoris* selectable marker HIS4; (iv) a kanamycin resistance gene; (v) a 3' AOX1 flanking fragment; (vi) and pBR322 elements enabling propagation and selection in *E. coli* hosts. The HIS4 marker is useful in selecting for positively transformed hosts and the kanamycin resistance gene is useful for selecting high copy number transformants. Cloning of the glycolate oxidase DNA is accomplished by restriction enzyme digestion of the vector and the glycolate oxidase containing DNA fragment with compatible restriction endonucleases, followed by a ligation according to protocols well known to those skilled in the art. Typically the result of such ligation is the creation of a vector in which the spinach glycolate oxidase gene is inserted between the AOX1 promoter and the AOX1 termination region. The resulting vector is capable of transforming any suitable *Pichia sp.* and effecting the expression of enzymatically-active glycolate oxidase and has been labeled pMP1.

Because the plasmid pMP1 lacks an origin of replication for Pichia, all transformants arise from chromosomal integration of the plasmid. The routiner will recognize, however, that a suitable transforming plasmid could also be constructed so as to be autonomously replicating within the transformed host. For the purpose of the present invention chromosomal integration of the plasmid is preferred, as it provides a more stable transformed host.

Transformation of a suitable *Pichia sp.* may be accomplished by a variety of protocols well known in the art. As previously mentioned, preferred Pichia hosts comprise Pichia auxotrophic mutants and most preferred is the his-mutant, GTS115 (his4) (NRRL Y-15851). Briefly, spheroplasts of the host strain GTS115 (his4) are first prepared using a yeast cell wall degrading enzyme followed by incubation with the transformation vector, pMP1. After plating on selective media, His+ transformants are isolated. His+ transformants may be further screened for specific replacement of chromosomal alcohol oxidase gene by glycolate oxidase gene by selecting for a slow growing phenotype on methanol Mut–. For the purpose of producing commercially useful quantities of glycolate oxidase it is advantageous to select clones with the highest possible copy number of the transforming plasmid. This is accomplished by growing the now Kan+ transformants in the presence of ever increasing levels of kanamycin and selecting the clones with the greatest tolerance to kanamycin.

Transformants, containing multiple copies of the glycolate oxidase gene under the control of the Pichia alcohol oxidase promoter are then evaluated for the production of enzymatically-active glycolate oxidase. Transformants are grown to an $A_{600}$ of 2–10 in MGY medium with shaking at 30° C. Cells are then pelleted and shifted to MM medium containing 0.5% methanol for induction and incubated with shaking at 30° C. for 1–4 days. Glycolate oxidase protein may be detected by Western blot analysis or glycolate oxidase activity may be detected by means of a spectrophotometric assay. Most preferred is the method described by Soda, et al., (1973) supra. This assay measures the glyoxylate produced by the glycolate oxidase-catalyzed oxidation of glycolate by reacting said glyoxylate with glycine and o-aminobenzaldehyde to form a yellow complex having an absorbance maximum at 440 nm. High copy number transformants designated *Pichia pastoris* strains GS115-MSP10 and MSP12 harboring multiple copies of the spinach glycolate oxidase-encoding DNA under expression control of the AOX1 promoter, have been deposited under the terms of the Budapest Treaty with the Northern Regional Research Laboratories and are designated by the accession numbers NRRL Y-21001 (deposited Sep. 24, 1992), and NRRL Y-21040 (deposited Dec. 28, 1992), respectively.

*P. pastoris* cells were typically prepared by growing an inoculum in 100 mL of YNB containing 1% glycerol. After 48 h growth at 30° C., the cells were transferred into a fermenter containing 10 L of media composed of yeast nitrogen base (YNB) without amino acids (134 g), glycerol (100 g), and biotin (20 mg). The fermentation was operated at pH 5.0 (controlled with $NH_4OH$), 30° C., agitation rate of 200 rpm, aeration of 5 slpm, 5 psig of air, and dissolved oxygen maintained at no lower than 50% saturation. When glycerol was depleted, the cells were induced to express glycolate oxidase by growth in the same media except that methanol (50 g) was substituted for glycerol. Glycolate oxidase activity during induction was followed by enzyme assay. After 24 h of induction the cells were harvested following treatment with glycerol (1 kg). Following harvest the cells were frozen in liquid nitrogen and stored at –80° C.

Unlike *A. nidulans*, *H. polymorpha* and *P. pastoris* cell transformants required permeabilization prior to use as catalyst for the oxidation of glycolic acid to glyoxylic acid. A variety of known methods of permeabilization were useful for preparing cells with sufficient glycolate oxidase activity (see Felix, H. *Anal. Biochemistry*, Vol. 120, 211–234, (1982)). Typically, a suspension of 10 wt % wet cells in 0.1% (v/v) "TRITON" X-100/20 mM phosphate buffer (pH 7.0) was mixed for 15 minutes, then frozen in liquid nitrogen, thawed, and washed with 20 mM phosphate/0.1 mM FMN buffer (pH 7.0). A second method of permeabilization was performed by mixing a suspension of 10 wt % wet cells in 0.1% (w/v) benzalkonium chloride (Sigma)/20 mM phosphate buffer (pH 7.0) for 60 minutes, then washing the permeabilized cells with 20 mM phosphate/0.1 mM FMN buffer (pH 7.0).

A fourth microbial cell catalyst which has been utilized in the present invention is a transformant of *Escherichia coli* (a bacteria) which expresses the glycolate oxidase enzyme from spinach, as well as an endogenous catalase. Such an *E. coli* transformant was prepared as described in Macheroux et. al, *Biochem. Biophys. Acta*, Vol. 1132, 11–16 (1992), and is additionally described in Example 5.

The glycolate oxidase (added as *Aspergillus nidulans, Pichia pastoris, Hansenula polymorpha* or *Escherichia coli* whole cells) used in the reaction should be present in an effective concentration, preferably about 0.1 to about 10 IU/mL. An IU (International Unit) is defined as the amount of enzyme that will catalyze the transformation of one micromole of substrate per minute.

The pH of the reaction solution should be between 7 and 10, preferably between 8.0 and 9.5. The pH can be maintained by a buffer, since enzyme activity varies with pH. The pH of the reaction decreases slightly as the reaction proceeds, so it is often useful to start the reaction near the high end of the maximum enzyme activity pH range, about 9.0–9.5, and allow it to drop during the reaction. As has been previously described in U.S. Pat. No. 5,219,745 (Jun. 15, 1993), an amine buffer capable of complexing the glyoxylic acid (by forming an amine which is more stable to chemical or enzymatic oxidation) is employed along with catalase to maximize product selectivity. Ethylenediamine, or less preferably, tris(hydroxymethyl)aminomethane (hereinafter TRIS), piperazine, or glycylglycine improved the yield of glyoxylic acid. These amines are used in a molar ratio of amine/glycolic acid (starting amount) of 1.0 to 3.0, preferably 1.0 to 1.33. Within this range, the exact value may be adjusted to obtain the desired pH. With very basic amines used at high amine to glycolic acid ratios, it may be necessary to adjust the pH, as by adding acid, for example hydrochloric or sulfuric acids. With less basic amines such as TRIS, it may be necessary to add a base to maintain the desired pH.

The concentration of accessible catalase (added as *Aspergillus nidulans, Pichia pastoris, Hansenula polymorpha* or *Escherichia coli* whole cells) should be 50 to 100,000 IU/mL of reaction mixture, preferably 350 to 14,000 IU/mL. It is preferred that both the glycolate oxidase and catalase enzymes be present within the same microbial cell (in this case, a transformant of *A. nidulans, P. pastoris, H. polymorpha* or *E. coli*), but an additional source of microbial catalase (for example, but not by way of limitation, *Saccharomyces cerevisiae* or the like) may be added to supplement the catalase present. Additionally, the catalase and glycolate oxidase concentrations should be adjusted within the above ranges so that the ratio (measured in IU for each) of catalase:glycolate oxidase is at least about 250:1. Flavin mononucleotide (FMN) is an optional added ingredient, used at a concentration of 0.0 to 2.0 mM, preferably 0.01 to 0.2 mM.

The reaction rate is at least partially controlled by the rate at which oxygen can be dissolved into the aqueous medium. Oxygen can be added to the reaction as the oxygen in air, but it is preferred to use a relatively pure form of oxygen, and to use elevated pressures. Although no upper limit of oxygen pressure is known, oxygen pressures up to 50 atmospheres may be used, and an upper limit of 15 atmospheres is preferred. Sparging (bubbling) oxygen through the reaction mixture is necessary to maintain a high oxygen dissolution (and hence reaction) rate. Oxygen is sparged through the reaction mixture at a rate of 0.05 to 5 volumes of oxygen (measured at atmospheric pressure) per volume of reaction mixture per minute (vol/vol min), and preferably between 0.2 and 2 vol/vol/min. Additionally, a convenient form of agitation is useful, such as stirring.

The reaction temperature is an important variable, in that it affects reaction rate and the stability of the enzymes. A reaction temperature of 0° C. to 40° C. may be used, but the preferred reaction temperature range is from 5° C. to 15° C. The reaction temperature should not be so low as to cause the reaction mixture to freeze. Operating in the preferred temperature range maximizes recovered enzyme activity at the end of the reaction.

Upon completion of the reaction and removal of the microbial cell transformant catalyst by filtration or centrifugation, the amine buffer is most conveniently removed by use of an ion exchange resin. Suitable acidic cationic exchange resins include "AMBERLITE" CG120 or "AMBERLITE" IR120 (Rohm & Haas Co.), and "DOWEX" 50 (Dow Chemical Co.). The amine may then be recovered and subsequently recycled by treatment of the resin with strong base.

The product glyoxylic acid is useful in the preparation of vanillin and ethylvanillin, as well as being used in ion exchange resins and as an acid catalyst in the pharmaceutical industry (Ullmanns). It is usually sold as a 50% (weight percent) aqueous solution. It is also to be understood that reference to glyoxylic acid in this application can also mean the glyoxylate anion, especially when the glyoxylic acid is present in a solution whose pH is greater than about 2.3.

Media for Microbial Cell Transformants Cultured in Shaker Flask or Fermenter

The minimal media (MIN) used for culturing the microbial cell transformants consisted of fructose (1%, 1.0 g/L), threonine (100 mM, 11.9 g/L), ammonium tartrate (6.0 g/L), trace elements (1 mL/L), and salt solution (10 mL/L); the pH of this minimal media was adjusted to 6.5 with sodium hydroxide.

The rich (SYG) media used for culturing the microbial cell transformants consisted of yeast extract (0.5%, 5.0 g/L), ammonium nitrate (100 mM, 8.0 g/L), potassium phosphate (monobasic, 33 mM, 4.5 g/L), magnesium sulfate heptahydrate (2 mM, 0.5 g/L), trace elements (1.0 mL/L); after adjusting the pH to 5.5 and autoclaving, glucose was added to 2% (w/v).

Glycolate Oxidase and Catalase Assays for Whole Cells

Microbial cell transformants were assayed for glycolate oxidase activity by accurately weighing ca. 5–10 mg of the wet cells (blotted on filter paper to remove excess moisture) into a 3-mL quartz cuvette containing a magnetic stirring bar and 2.0 mL of a solution which was 0.12 mM in 2,6-dichlorophenolindophenol (DCIP) and 80 mM in TRIS buffer (pH 8.3). The cuvette was capped with a rubber septum and the solution deoxygenated by bubbling with nitrogen for 5 min. To the cuvette was then added by syringe 40 $\mu$L of 1.0M glycolic acid/1.0M TRIS (pH 8.3), and the mixture stirred while measuring the change in absorption with time at 605 nm ($\epsilon$=22,000).

Catalase activity was assayed by accurately weighing ca. 2–5 mg of the wet cells into a 3-mL quartz cuvette containing a magnetic stirring bar and 2.0 mL of a distilled water, then adding 1.0 mL of 50 mM hydrogen peroxide in 50 mM phosphate buffer (pH 7.0) and measuring the change in absorption with time at 240 nm ($\epsilon$=39.4). Glycolate oxidase and catalase activities of the *Aspergillus nidulans* wet cells cultured in different media ranged from 0.5–2.0 DCIP IU/gram for glycolate oxidase and 500–7000 IU/gram for catalase. Glycolate oxidase and catalase activities of the *E. coli* wet cells (unpermeabilized) cultured in different media ranged from 0.8–4.0 DCIP IU/gram wet cells for glycolate oxidase and 1000–2000 IU/gram wet cells for endogenous catalase. Glycolate oxidase and catalase activities of the *H. polymorpha* or *P. pastoris* wet cells (permeabilized) cultured in different media ranged from 20–120 DCIP IU/gram wet cells for glycolate oxidase and 30,000–200,000 IU/gram for endogenous catalase.

HPLC Analysis for Glycolic, Glyoxylic, Oxalic, and Formic Acid

Samples for analysis were first filtered through a Millipore Ultrafree MC filter unit (10,000 mw cutoff). Analyses for glycolic acid, glyoxylic acid, oxalic acid and formic acid were performed by high performance liquid chromatography (HPLC) on a Bio-Rad Aminex HPX-87H column (300× 7.8 mm) at 40° C., using as solvent an aqueous solution of $H_2SO_4$ (0.01N) and 1-hydroxyethane-1,1-diphosphonic acid (0.1 mM) at 1.0 mL/minute. UV analysis was performed at 210 nm. The retention times of oxalic acid, glyoxylic acid, glycolic acid, formic acid, and propionic acid (internal standard) or isobutyric acid (internal standard) were 4.29, 6.09, 7.77, 8.79, 11.41, and 13.05 minutes, respectively.

EXAMPLE 1

Aspergillus Host Strain Selection

As a preliminary step in the construction of a glycolate oxidase-producing Aspergillus strain, available host strains were examined for endogenous levels of catalase activity, and the strain exhibiting highest catalase activity was selected to serve as expression host.

In particular, catalase activity was examined in both an argB *Aspergillus niger* strain 350.52 (ATCC 20739), and an *Aspergillus nidulans* strain T580, which is pyr⁻ and harbors multiple copies of the alcR gene. Cultures of each host strain were grown at the 10 liter scale for 48 hours in either minimal medium or rich (SYG) medium (salts, yeast extract, glucose) under inducing conditions. For the *A. nidulans* strains T580, this entailed growth in 3% SYG (with 3% glucose) until glucose levels were minimal, after which the medium was supplemented with the inducer methylethylketone. Mycelia (500–700 g) was harvested 16–20 hours after induction. The *A. niger* strain was grown in SY medium (salts, yeast extract) containing 2% corn starch for 40 hours.

An aliquot (100 mL) of each sample was disrupted with glass beads (0.5 mm) in a DyanoMill vessl for 120 sec, and the refrigerated disruptate was then assayed for catalase activity, using an assay of conventional design, Beers et al., *J. Biol. Chem.,* vol. 195, 133 (1952). Results revealed that the catalase levels in the *A. nidulans* host strain T580 were 110 IU/mg. Catalase levels in the *A. niger* strain were found to be 90 IU/mg. On this basis, the *A. nidulans* strain was selected to serve as glycolate oxidase production host.

EXAMPLE 2

Isolation of cDNA Coding for Spinach Glycolate Oxidase

For expression in an Aspergillus species host, DNA coding for spinach glycolate oxidase was first isolated from a library of spinach cDNA. More particularly, poly(A)-containing mRNA was collected from fresh, young spinach leaves using the phenol extraction method and protocols conventional thereto. Complementary DNA was then prepared against the mRNA using the reverse transcriptase-based method and standard protocols.

Based on knowledge of the cDNA sequence coding for spinach glycolate oxidase, as reported by Volokita and Somerville, *J. Biol. Chem.,* vol. 262, 15825 (1987), the polymerase chain reaction (PCR) approach was used to amplify selectively the glycolate oxidase-encoding DNA resident in the library. In particular, and as shown schematically in FIG. 2, glycolate oxidase-encoding cDNA was amplified in three ligatable sections, using oligonucleotide primers specific for the following regions of the target cDNA; (1) a 203 bp N-terminal region encompassing the ATG initiation codon and including the BglII site 203 bp 3' thereof; (2) a 565 bp central region encompassing the BglII site and including the SacI site; and (3) a 342 bp C-terminal region encompassing the SacI site and the stop codon TAA. As will be noted in FIG. 2, cloning and assembly of the intact coding region was facilitated by the use of primers having non-hybridizing 5' flanks which incorporated a selected restriction site (denoted using the conventional single letter, restriction site designation). Protocols conventional to polymerase chain reaction were employed.

PCR-amplified regions of the cDNA were sequence-verified and assembled into the vector pTZ19R, using the strategy shown in FIG. 2. The correct sequence in the assembled construct was also confirmed.

Figure 3:
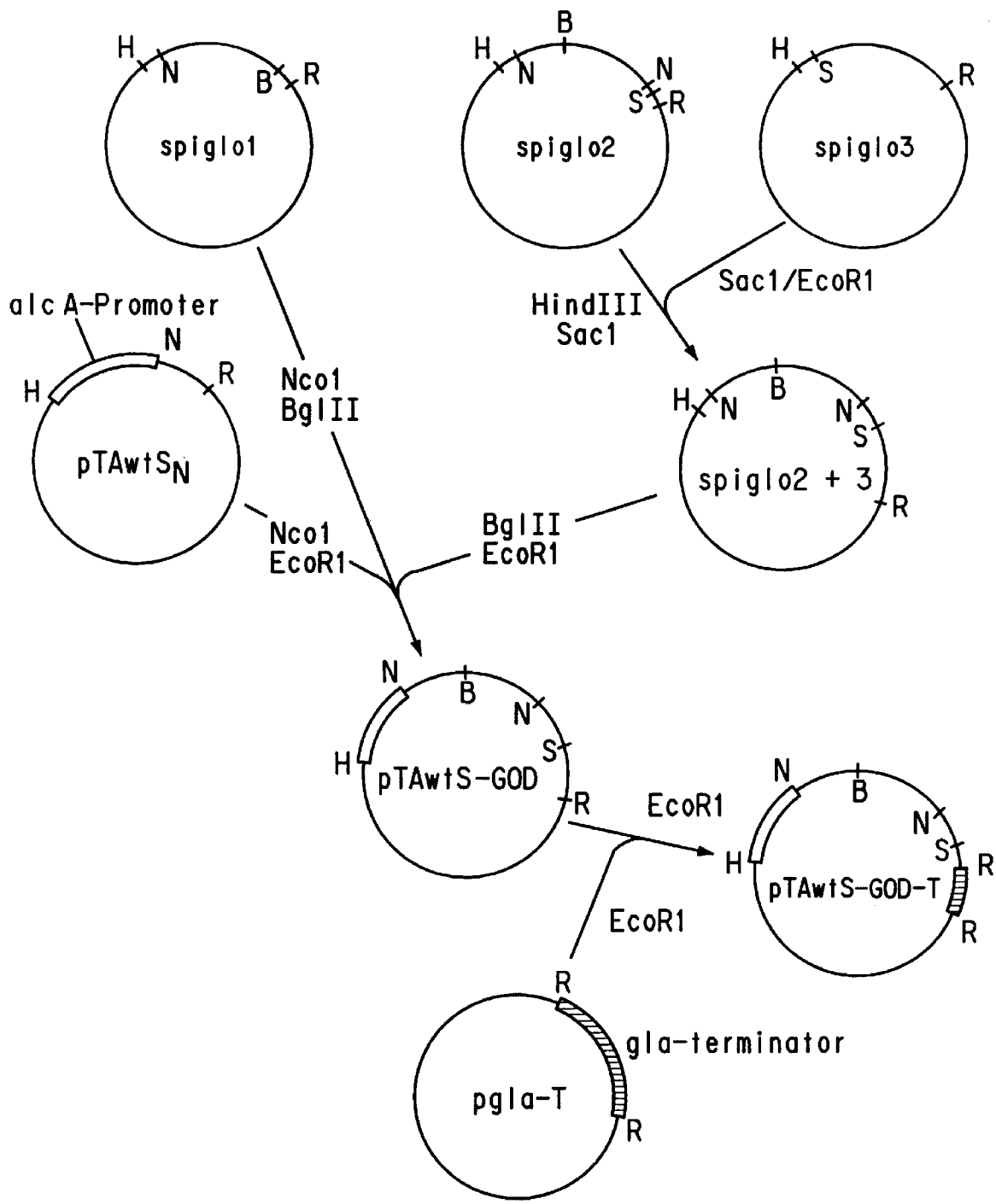
FIG. 3 illustrates schematically the steps in constructing a recombinant DNA expression construct to achieve production of glycolate oxidase in an Aspergillus host.

For Aspergillus strain construction, cDNA coding for spinach glycolate oxidase, obtained as just described, was linked operably with the expression controlling region of the alcohol dehydrogenase I (alcA) gene of *Aspergillus nidulans,* using the strategy illustrated schematically in FIG. 3. The particular vector chosen, designated pTAwtS, is described by Gwynne et al., *Biochem. Soc. Transactions,* vol. 17, 338 (1989), which is incorporated herein by reference. Briefly, this vector incorporates, in a pUC8 background, a 2.2 kb HindIII fragment of the *A. nidulans* alcA gene which incorporates all DNA elements required for proper translation and regulated transcription of protein-encoding DNA linked downstream thereof. The particular vector pTAwtS incorporates an engineered NcoI site precisely at the initiation codon downstream of the expression controlling region, to accept in proper translational reading frame a DNA molecule coding for the protein of interest. The vector pTAwtS was further modified by incorporation at a site downstream of the cloning site, a transcriptional terminator derived from the *Aspergillus niger* glucoamylase gene (gla), in the form of a 2.2 kb EcoRI/EcoRI DNA fragment. Thus, as shown in FIG. 3, the intact cDNA clone coding for spinach glycolate oxidase, was incorporated as a BglII/EcoRI fragment into NcoI/EcoRI-cleaved pTAwtS to form pTAwtS-GOD. The transcriptional terminator was then introduced into the EcoRI site 3' of the stop codon resident in the glycolate oxidase coding region to yield pTAwtS-GOD-T. Sequencing across restriction site junctions confirmed that the construct contained the desired functional components in the proper relationship.

For expression, there was selected as host a strain of *Aspergillus nidulans* designated T580, which is pyr⁻ and harbors multiple copies of the gene alcR, the expression product of which co-regulates expression from the alcA promoter. Construction of the T580 host, from the pyr⁻ *A. nidulans* strain was achieved as described by Felenbok et al., *Gene,* vol. 73, 385 (1988), which is incorporated herein by reference. The plasmid pTAwtS-GOD-T was introduced into T580 using now conventional DNA-mediated transformation protocols, described for example by Yelton et al., *Proc. Natl. Acad. Sci.,* vol. 81, 1470 (1984). Briefly, spheroplasts of the host strain T580 were first prepared using the cell wall degrading enzyme Novozyme 234. Spheroplasts were then incubated in the presence of calcium/polyethylene glycol, with about 10 ug of pTAwtS-GOD-T and 2 ug of a marker plasmid carrying the pyr4 gene of *Neurospora crassa.* After plating on medium lacking uridine, transformants (about 20 in all) were selected and then subjected to Southern blot analysis by probing with radiolabelled glycolate oxidase-encoding DNA, to confirm the presence of genomically integrated DNA coding for glycolate oxidase. Southern blot analysis revealed that about 80% of the transformants harboured multiple copies of the spinach glycolate oxidase encoding gene.

Transformants harboring multiple copies of the glycolate oxidase gene were then evaluated individually for glycolate oxidase activity. This was done by introducing conidial inoculum prepared from individual transformants into 50 mL of minimal fungal medium which contains salts and 0.2% fructose/1% threonine (as inducer) combination. After culturing at 30° C. for 48 hours, cell extracts were analyzed for glycolate oxidase activity, using the o-aminobenzaldehyde assay (Soda et al.; see above). In this assay, with absorbance monitoring at 440 nm, several of the transformants tested positive for glycolate oxidase activity, and one transformant, designated *Aspergillus nidulans* strain T17 was selected.

A sample of *Aspergillus nidulans* strain T17, harboring multiple copies of the spinach glycolate oxidase-encoding DNA under expression control of the *A. nidulans* alcA promoter, and multiple copies of the *A. nidulans* alkR gene, the product of which regulates function of the alcA promoter, was deposited under the terms of the Budapest Treaty with the Northern Regional Research Center, Peoria, Ill., U.S.A. on Sep. 24, 1992, under NRRL No. 21000.

EXAMPLE 3

Preparation of *Hansenula polymorpha* Transformants

Construction of Expression Vector pFMDGO.

The GO gene as found in pDA-PCR#1, which is derived from the Aspergillus transformation plasmid pTAwtS-GOD, was excised using EcoRI and BamHI. More specifically, pTAwtS-GOD contains a spinach glycolate oxidase gene under the control of a *Aspergillus nidulans* alcA promoter and bounded at the 5' end by a BglII site and at the 3' end by an EcoRI site. The glycolate oxidase gene in pTAwtS-GOD is amplified by conventional PCR protocols using primers which incorporated an XbaI site at one end and an EcoRI site at the opposite end. The PCR fragment is ligated between the XbaI and EcoRI sites in the Bluescript plasmid (Stratagene, La Jolla, Calif.) to give the plasmid pDA-PCR#1. For a more detailed description of this procedure see International Patent Application WO 95/01444 (publication date: 12 Jan., 1995), herein incorporated by reference for such purpose.

The restricted fragment was cloned into the multiple cloning site of the basic vector pFPMT130 (see FIG. 4) using the EcoRI and the BamHI site for insertion. Restriction and ligations, propagation and isolation of the newly generated plasmid DNA followed standard procedures as described by Maniatis et al. 1982. The insertion of the cDNA sequence resulted in the expression vectors pFMDGO (FIG. 6).

Construction of Expression Vector PRBGO.

A second series was constructed in the pRB vector harboring an chloramphenicol resistance sequence as a selection marker (FIG. 5). The GO gene as found in pDA-PCR#1 was excised using EcoRI and BamHI. The restricted fragment was cloned into the multiple cloning site of the vector pRB (FIG. 5) using the EcoRI and the BamHI site for insertion. Restriction and ligations, propagation and isolation of the newly generated plasmid DNA followed standard procedures as described by Maniatis et al., 1982. The insertion of the cDNA sequence resulted in the expression vector pRBGO (FIG. 7).

Transformation of *H. polymorpha* with pFMDGO.

The vector pFMDGO was used to transform competent *H. polymorpha* cells of strain RB11, deficient in ortidin 5' phosphate dehydrogenase (ura⁻). The auxotrophic strain RB11 was generated basically as described by Roggenkamp et al., 1986. Competent cells of this strain are generated according to established protocols (Dohmen et al., 1991) as follows: 10 mL yeast medium (YPD) were inoculated with cells and cultured at 37° C. overnight. This culture was subsequently used to inoculate 200 mL of YPD. Cells were grown at 37° C. to an $OD_{600}$ of 0.6 to 1.0. Cells were harvested by centrifugation, washed at room temperature in 100 mL of a solution A (1M sorbitol, 10 mM bicine pH 8.35 3% ethylene glycol) and then resuspended in 4 mL of solution A; 11 L DMSO were added and the competent cells were stored at −70° C.

For transformation 10 g of plasmid DNA and 100 mL of cold 0.1M $CaCl_2$ were added to the frozen cell aliquots; after fast thawing 1.0 mL of a solution B (40% PEG 3350, 200 mM bicine pH 8.35) was added, the transformation mixtures was incubated at 37° C. for 1 hour. Subsequently cells were washed in 1 mL of a solution C (150 mM NaCl, 10 mM bicine pH 8.35) and resuspended in 200 L. This suspension was plated on selective agar plates (YNB-glucose). Plates were incubated at 37° C. for 3 to 5 days.

Mitotically stable strains with multimeric copies of the heterologous DNA were generated by passage stabilization. Colonies from developed plates were used to inoculate 3 mL of YNB glucose and cultured at 37° C. A 50 L aliquot of the fully grown culture was used to inoculate another 3 mL culture. This procedure was repeated for some 40 generations of growth. During this passaging plasmid DNA was integrated into the genome. Subsequently 3 mL of YPD (non-selective medium) was inoculated and cultured at 37° C. Diluted aliquots of passage stabilized cells resulted in an identical number of colonies when plated on selective and non-selective agar plates.

The passaged transformants were used to inoculate 3 mL of YNB supplemented with 1% glycerol. After two day of growth the cells were transferred to 3 mL YNB supplemented with 1% methanol. After a further day of induction cells were harvested by centrifugation (5 min. at 800× g). Harvest cells were resuspended in 600 mL of extraction buffer (1 mM DTT, 0.1 mM FMN, 10 mM PMSF, 10% DMSO in 0.1 sodium phosphate buffer pH 8.3). Cells were broken with glass beads (0.45–0.5 mn diameter for 5 minutes cooling with $CO_2$ every 30 seconds. Cell debris was removed by centrifugation (15 minutes at 15000× g at 4° C.). Glycolate oxidase activity was measured from cell lysates using a spectrophotometric assay (with absorbance monitoring at 440 nm) for GO enzyme activity employing o-aminobenzaldehyde and glycine (Soda et al., 1973). Results are summarized in Table 3 with activities being reported per mg of protein.

TABLE 3

| pFMDGo transformed RB11 strain No. | GO activity mU/mg |
| --- | --- |
| 11.2.01 | 1042 |
| 11.2.02 | 709 |
| 11.2.08 | 772 |
| 11.2.12 | 124 |
| 11.2.14 | 2047 |
| 11.2.16 | 1855 |
| 11.2.17 | 2910 |
| 11.2.18 | 1504 |
| 11.2.21 | 945 |
| 11.2.23 | 467 |
| 11.2.24 | 281 |
| 11.2.26 | 270 |

Transformation of *H. polymorpha* with pRBGO.

The vector pRBGO was used to transform competent *H. polymorpha* cells of strain RB11, essentially as described for pFMDGO, above. After passage stabilization and assay for glycolate oxidase activity the following clones were selected:

TABLE 4

| pRBGO transformed RB11 strain No. | GO activity mU/mg |
| --- | --- |
| 11.11.80 | 5958 |
| 11.11.89 | 3055 |
| 11.11.95 | 4281 |
| 11.11.109 | 3771 |
| 11.11.126 | 7524 |
| 11.11.165 | 3583 |
| 11.11.177 | 4480 |
| 11.11.178 | 4492 |
| 11.11.179 | 3689 |

One strain 11.11.126 was selected for further subcloning, and the results are shown in Table 5.

TABLE 5

| Subclones of 11.11.126 strain No. | GO activity mU/mg |
| --- | --- |
| 11.11.126.1 | 4111 |
| 11.11.126.2 | 71 |
| 11.11.126.3 | 3495 |
| 11.11.126.4 | 0 |
| 11.11.126.5 | 2266 |
| 11.11.126.6 | 5092 |
| 11.11.126.7 | 7026 |
| 11.11.126.8 | 4187 |
| 11.11.126.9 | 3274 |
| 11.11.126.10 | 4232 |

The best strain from this subcloning, 11.11.126.7, was selected and designated *Hansenula polymorpha* GO1 and deposited on Mar. 30, 1993 under the terms of the Budapest Treaty with U.S. Department of Agriculture, Northern Regional Research Laboratories, located in Peoria, Ill., and is designated by the accession number NRRL No. Y-21065. The copy number of the integrated heterologous DNA was determined for *Hansenula polymorpha* GO1 as outlined by Gellissen et al., 1992. DNA was isolated from the transformant and from the untransformed host strain RB11. The isolated DNA was restricted with Asp718/SalI, transferred to nitrocellulose and hybridized to a $^{32}$P-labeled EcoRI/Asp718 fragment. This results in two signals in similar electrophoretic positions for the genuine single copy FMD gene and the heterologous FMD promoter/GO fusion. In DNA dilutions the copy number was estimated comparing the signal intensity of the heterologous fragments with that of the intrinsic single copy control. This determination revealed that the *Hansenula polymorpha* GO1 contains approximately 30 copies of the integrated plasmid. This recombinant strain is mitotically stable and remains unchanged during fermentation.

EXAMPLE 4

Preparation of *Pichia pastoris* Transformants
Materials and methods.

The plasmids pHIL-D4 and pHIL-S1 were obtained from the Phillips Company (Phillips Petroleum Company, Bartlesville, Okla.). PCR reagents were obtained from and used according to Perkin-Elmer Cetus. Protocols conventional to PCR were employed as described in Innis, M. et al., PCR Protocols 1990. Academic Press. Restriction enzyme digestions, ligations transformations and plasmid preparations were done as described in Sambrook, J., et al., Molecular Cloning: a laboratory manual. 1989. Cold Spring Harbor Laboratory Press.

Construction of plasmid pMP1 containing spinach alycolate oxidase gene.

For the construction of a vector capable of transforming *Pichia sp.* for the expression of glycolate oxidase, the glycolate oxidase (GO) gene located in the vector pDA-PCR#1 (FIG. 8) was used. pDA-PCR#1 is derived from the Aspergillus transformation plasmid pTAwtS-GOD which is fully described in International Patent Application WO 95/01444 (publication date: 12 Jan., 1995), herein incorporated by reference for such purpose. Briefly, pTAwtS-GOD contains a spinach glycolate oxidase gene under the control of a *Aspergillus nidulans* alcA promoter and bounded at the 5' end by a BglII site and at the 3' end by an EcoRI site, (FIG. 8). The glycolate oxidase gene in pTAwtS-GOD was amplified by conventional PCR protocols using primers which incorporated an XbaI site at one end and an EcoRI site at the opposite end. The PCR fragment was ligated between the XbaI and EcoRI sites in the Bluescript plasmid (Stratagene, La Jolla, Calif.) to give the plasmid pDA-PCR#1. (FIG. 8)

The GO gene as found in pDA-PCR#1 was amplified by polymerase chain reaction (PCR) using primers incorporating EcoRI restriction sites (MP18: 5' TAC CGA ATT CAT GGA GAT CAC AAA TGT G 3' (SEQ. ID NO.: 2) and MP19: 5' AAC AGA ATT CTT ATA ATC TGG CAA CAG A 3' (SEQ. ID NO.; 3)).

Plasmid pHIL-D4 is commercially available from Phillips Co. (Phillips Petroleum Company, Bartlesville, Okla.) and is a shuttle vector designed for integration in *Pichia pastoris*. Briefly, this vector incorporates a 1100 bp methanol inducible promoter AOX1 which is connected through an EcoRI site to a 300 bp AOX1 transcriptional termination element. Also on the plasmid are a *P. pastoris* selectable marker HIS4, a kanamycin resistance gene, a 3' AOX1 flanking fragment and elements allowing propagation and selection in *E. coli* hosts. (FIG. 8). The amplified GO gene was digested with EcoRI and subcloned into pHIL-D4 at the EcoRI site (between AOX1 promoter and AOX1 termination) in the forward orientation to produce plasmid pMP1 (FIG. 8). pMP1 was then use to transform *Pichia pastoris*.

Transformation of *Pichia pastoris* with pMP1.

A host strain of *Pichia pastoris* designated GTS115 (his4), (Phillips Petroleum Company, Bartlesville, Okla.) was selected for transformation by pMP1. pMP1 was introduced into GTS115 (his4) using conventional DNA-mediated transformation protocols described by Phillips. (Cregg et al., *Mol. and Cell. Biol.*, vol. 5, 3376–3385, (1985)).

Figure 9:
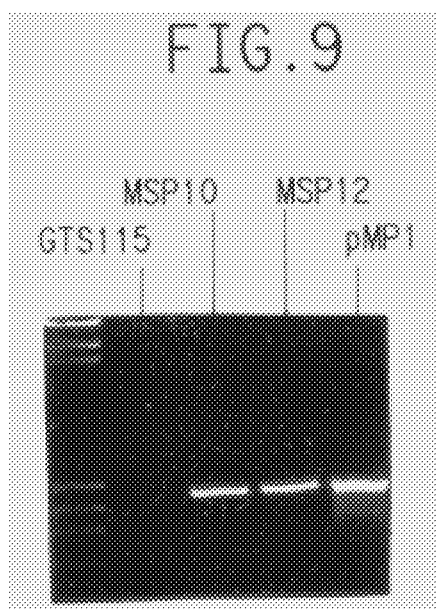
FIG. 9 is a gel electrophoresis of PCR detection of the glycolate oxidase gene from strains GS115-MSP10 and MSP12.

Briefly, spheroplasts of the host strain GTS115 were first prepared using the cell wall degrading enzyme zymolase (Sigma Chemical, St. Louis, Mo.). Spheroplasts were then incubated in the presence of sorbitol/polyethylene glycol, with about 1–2 ug of linearized pMP1. Transformants were allowed to regenerate on media selective for His+ prototrophs. His+ clones were screened for chromosomal AOX1 displacement by replica plating on media with or without 0.5% methanol and selecting clones with a slow growing phenotype on methanol (Mut–). Mut– clones were further screened for expression cassette copy number by selective growth in media containing increasing levels of kanamycin (from 100 ug/ml to 1000 ug/ml). Two clones exhibiting the greatest resistance to kanamycin were selected and labeled GS115-MSP10 and MSP12. GS115-MSP10 and MSP12 tolerated >1000 ug/ml kanamycin whereas 15 other His+/Mut– clones did not grow in kanamycin >100 ug/ml. PCR with primers MP18 (SEQ ID #2) and MP19 (SEQ ID #3) of chromosomal DNA isolated from GS115-MSP10 and MSP12 resulted in a 1.1 kb fragment indicating the presence of GO gene in these recombinant strains and indicated in FIG. 9.

Expression of active glycolate oxidase from MSP10 and MSP12.

Figure 10:
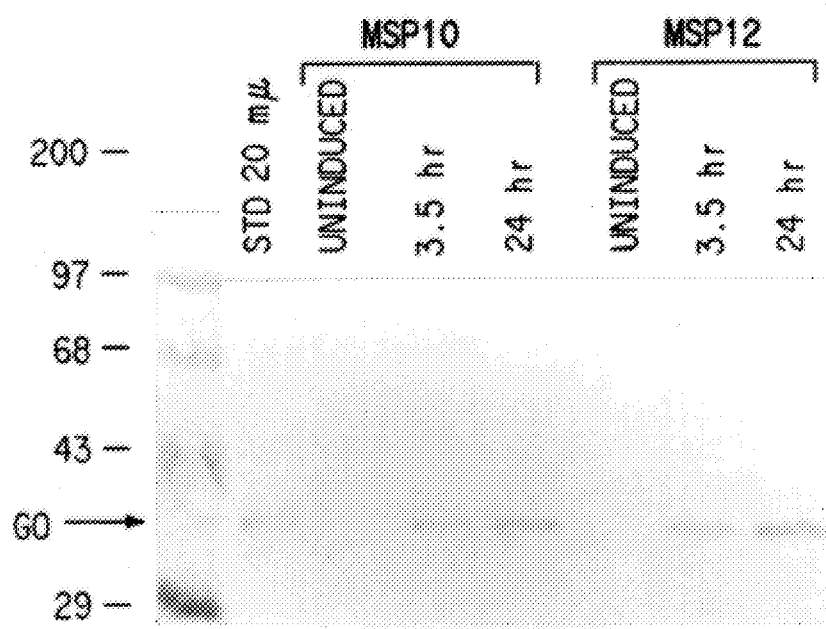
FIG. 10 is a Western blot analysis of glycolate oxidase protein production from transformed strains GS115-MSP10 and MSP12.

Strains GS115-MSP10 and MSP12 harboring multiple copies of the glycolate oxidase gene were evaluated individually for glycolate oxidase activity. This was done by growing GS115-MSP10 and MSP12 in appropriate media followed by induction with 0.5% methanol. Briefly, cells are grown to an $A_{600}$ of 2–10 in MGY medium (1.34% yeast nitrogen base without amino acids, 0.00004% biotin, 1% glycerol) with shaking at 30° C. Cells are then pelleted and shifted to MM medium (1.34% yeast nitrogen base without amino acids, 0.00004% biotin, 0.5% methanol) and incubated with shaking at 30° C. for 1–4 days. Cells were harvested at 0, 3.5 and 24 hrs post induction and lysed by vortexing with an equal volume of 0.5 mm glass beads in 50 mM sodium phosphate pH 7.4, 1 mM PMSF, 1 mM EDTA, 5% glycerol and 0.01 mM FMN for a total of 4 min in increments of 30 sec followed by 30 sec on ice. Detection of GO enzyme by Western blot analysis of these lysates confirmed the expression of GO gene in these strains. (FIG. 10)

Figure 11:
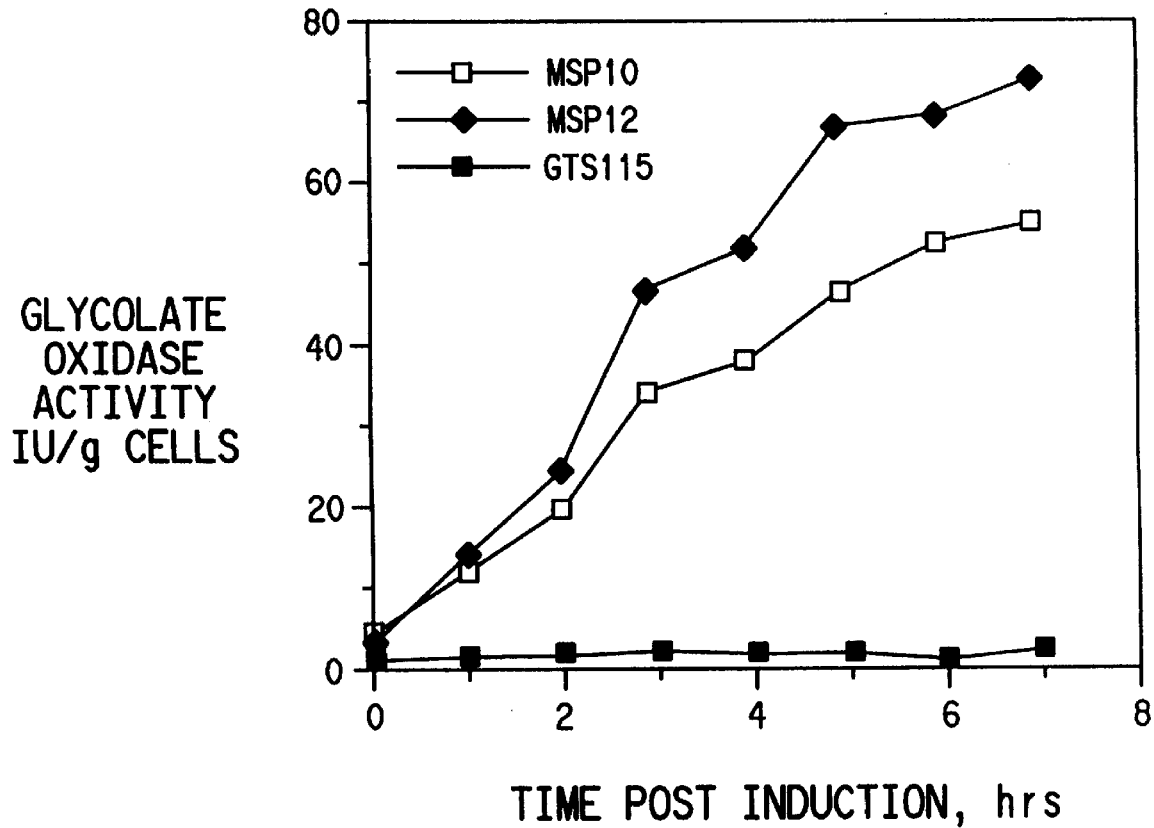
FIG. 11 is a graphic representation illustrating glycolate oxidase activity from induced cultures of transformed strains GS115-MSP10 and MSP12.

Additionally, glycolate oxidase activity was measured from cell lysates using a spectrophotometric assay (with absorbance monitoring at 440 nm) for GO enzyme activity employing o-aminobenzaldehyde and glycine (Soda, K., 1973) which demonstrated activities of 100–300 IU/g blotted cells. FIG. 11 illustrates a typical time course of glycolate oxidase activity after induction by methanol.

A sample of *Pichia pastoris* strains GS115-MSP10 and MSP12 harboring multiple copies of the spinach glycolate oxidase-encoding DNA under expression control of the AOX1 promoter, have been deposited under the terms of the Budapest Treaty with the Northern Regional Research Laboratories and are designated by the accession numbers NRRL Y-21001 and NRRL Y-21040 (deposited on Dec. 28, 1992), respectively.

Expression of endogenous catalase from MSP12 and GS115-MSP10.

Transformants GS115-MSP10 and MSP12 harboring multiple copies of the glycolate oxidase gene were evaluated individually for the ability to co-express endogenous catalase with enzymatically active glycolate oxidase. Briefly, cells were grown in shaker flasks for about 48 hrs to an $A_{600}$ of 2–10 in YNB medium with 1% glycerol at 30° C. Cells were then pelleted and shifted to fresh YNB medium containing 0.5% methanol (for induction) and incubated at 30° C. for an additional 16–24 hrs. For analysis, extracts of cells were prepared by transferring 100 mg of wet cells (blotted to remove excess moisture) to 1 ml of 50 mM sodium phosphate pH 7.4, 1 mM PMSF, 1 mM EDTA, 5% glycerol and 0.01 mM FNM and vortex mixing at high speed for 2 min in the presence of 1 g of 0.5 mm glass beads. Lysate was assayed for the presence of both catalase and glycolate oxidase.

Optionally, cultures were grown in 10 L fermenters with agitators for about 48 hrs. to an $A_{600}$ of 2–10 in YNB with 1% glycerol at 30° C. Cells were exposed to fresh medium containing 0.5% methanol (for induction) and allowed to incubate for an additional 6 hrs. Cells were then harvested and lysed as described above and the lysate assayed for the presence of both glycolate oxidase and endogenous catalase.

Glycolate oxidase was measured according to the method of Soda et al. as described above. Catalase activity was measured according to the method of Beers et al., *J. Biol. Chem.*, 195, 133 (1952). In this method samples suspected of containing catalase are mixed with an excess of hydrogen peroxide and absorbance is measure on an ultraviolet spectrophotometer at a wavelength of 240 nm. Table 6 illustrates co-expressed catalase and glycolate oxidase activities.

TABLE 6

| Strain | Hours Post-induction | G.O. activity | | Catalase activity | |
|---|---|---|---|---|---|
| | | IU/g Blotted cells | IU/mg Total Protein | IU/g Blotted cells | IU/g Total Protein |
| MSP10 | 22 | 158 | 7.3 | 91147 | 4220 |
| MSP12 | 22 | 180 | 5.7 | 123761 | 3904 |

As can be seen in Table 6, both catalase and glycolate oxidase can be effectively co-expressed by the strains MSP10 and MSP12.

EXAMPLE 5

Preparation of *Escherichia coli* Transformant

Materials

Restriction enzymes.

NcoI and PstI were from Bethesda Research Laboratories, Gaithersburg, Md. (BRL). BamHI and EcoRI were from Toyobo, Japan and BclI was from Boehringer, Indianapolis, Ind.

Antibiotics.

Ampicillin, kanamycin and chloramphenicol were from Sigma, St. Louis, Mo.

Growth media.

Yeast extract and bacto-tryptone were from Difco, Detroit, Mich., Glycerol (NB grade) was from Boehringer.

Other enzymes.

T4 DNA ligase was from BR1, and horseradish peroxidase was from Sigma. Sequenase was obtained from US Biochemicals, Cleveland, Ohio.

Chemicals, o-Dianisidine, flavin mononucleotide (FMN), isopropal-β-D-thiogalactopyranoside (1PTG) and phneylmethane-sulfonyl fluoride (PMSF) were from Sigma. Glycolic acid was from Aldrich, St. Louis, Mo.

Methods

Construction of the expression plasmid.

All restriction enzyme digestions, ligations and other common DNA manipulations, unless otherwise stated, were performed by standard procedures. The cDNA clone of glycolate oxidase (GAO) contained in plasmid PGAO was recovered by digestion with EcoRI and subsequent isolation of the small 1400 bp fragment by agarose electrophoresis (1%) and electroblotting on DEAL cellulose (Schleicher & Schült, NA 45. The GAO gene was then cloned into the EcoRI site of plasmid (+) pBluescript (Stratagene, La Jolla, Calif.) and the orientation of the inserted gene was checked by digestion with PsiI. In order to clone the GAO gene into the expression plasmid pET-3d it was necessary to introduce NcoI and BclI restriction sites at the 5' and 3' ends, respectively. The mutagenesis was performed with the Amersham mutagenesis system, version 2 (Amersham Corporation, Arlington Heights, Ill.) and all steps were carried out as described in the protocol. The two silent mutations were introduced in two consecutive mutagensis experiments. The sequence of the entire gene was then verified by single-strand dideoxy sequencing using the Sequenase sequencing system (USB, Cleveland, Ohio). The plasmid, isolated by *E. coli* strain GM119, was then digested with BclI and partially with NcoI; the 1150 bp fragment, containing the full length sequence of the GAO gene, was isolated as described above. Plasmid pET-3d was digested with NcoI and BamHI and the large fragment was isolated and purified in the same way. The silently mutated GAO gene was now inserted into the NcoI-BamHI restriction fragment of the expression vector using T4 DNA ligase.

Microbiological manipulations.

TB-medium was used for all bacterial cultures. Where required ampicillin (100 μg/ml) and chloramphenicol (50 μg/ml) were added. Plasmid pBluescript was propagated in *E. coli* strain XL1:blue or strain GM119. Strain IIMS174 was used to propagate plasmid pPM1 and strain BL21 (DE3)/pLsyS was used for expression of the spinach glycolate oxidase. All necessary transformations were carried out with the calcium chloride method as described in the literature. Single-strand DNA for sequencing and the mutagenesis experiments was produced by infecting XL1:blue transformants with the helper phage M13KO7 using standard procedures.

Purification of GAO derived from *E. coli*.

Cells from a 1 l growth were harvested by centrifugation at 20000× g for 20 min and the pellet was resuspended in 30 ml 0.1M Tris buffer (pH 8), containing 1 mM EDTA, 0.5 mM FMN and 0.5 mM PMSF. The cells were immediately frozen and stored at −20° C. for at least 15 h and then thawed. Due to the presence of lysozyme in the cells, freezing and thawing was an efficient method of achieving complete lysis. The viscosity of the resulting lysate, owing to the presence of uncleaved DNA, was reduced by adding DNase to a final concentration of 3 μg/ml and incubated for 60 min at 25° C. This crude extract was centrifuged at 40000× g for 30 min and the supernatent decanted and dialyzed against three changes of 115 mM Tris buffer (pH 8.3), containing 1 mM EDTA. The enzyme was then purified on hydroxyapatide and Q-sepharose as described previously. Details of a typical preparation are summarized in Table 7.

TABLE 7

Purification of spinach glycolate oxidase expressed in *Escherichia coli*

| Purification step | Volume (ml) | Protein content[b] (mg/ml) | Activity[c] (ΔOD/ min) | Specific activity (Δ/min × OD$_{280}$) | Yield (%) | Purification (n-fold) |
|---|---|---|---|---|---|---|
| Crude extract[a] | 35 | 27.5 | 0.18 | 0.007 | 100 | 1 |
| Dialysis | 40 | 24 | 0.15 | 0.00625 | 95 | 0.9 |
| Hydroxyapatite (pool) | 18 | 3.36 | 0.234 | 0.066 | 67 | 10 |
| Q sepharose (pool) | 1.5 | 0.73 | 2.2 | 3 | 52 | 430 |

[a]Crude extract was prepared from 14 g of sells, Expression of GAO was induced at $OD_{600}^{-1}$ and cells were harvested after 4 h.
[b]Protein concentration was estimated by assuming that an $OD_{280}$ of 1 equals 1 mg/ml protein.
[c]Activity was determined by using the enzyme coupled assay described in Example 5

Enzyme assay.

Glycolate oxidase activity was measured in an enzyme-coupled assay using horseradish peroxidase and o-dianisidine to utilize hydrogen peroxide generated during oxidation of glycolate. A typical assay mixture contained 10 μl of horseradish peroxidase (1 mg/ml), 50 μl of o-dianisidine solution (8 mM, 20% Triton X-1000, 10 μl of 1M sodium glycolate, and 930 μl of 0.1M potassium phosphate buffer (pH 8.3). The reaction was started by adding 10 μl of the glycolate oxidase sample. Formation of the o-dianisidine radical cation ($F_{440}$–11600$M^{-1}$ $cm^{-1}$), which reflects the catalytic activity of glycolate oxidase, was monitored at 440 nm and at 25° C.

EXAMPLE 6

Into a 20-mL pressure reaction bottle (Lab Glass #LG-3921-100) was placed 1.0 mL of a solution containing glycolic acid (0.750M), ethylenediamine (0.866M), propionic acid (0.075M), and flavin mononucleotide (0.01 mM); the pH of this solution (ca. 9.2) was not adjusted. The solution was cooled to 5° C., then 200 mg of frozen *Aspergillus nidulans* T17 cells grown in different media were added to the bottle. The bottle was fitted with a crown cap and septum (Lab Glass #LG-3922-100), and then pressurized to 70 psig and vented five times at 5° C. with pure oxygen using a 22 gauge needle, then pressurized to 70 psig (483 kPa) with oxygen and the needle removed. The cap was checked for leaks by briefly submerging the tube in cold water and looking for gas bubbles, then wiped dry and placed upright in a test tube rack attached to the top of a rotary shaker. The contents of the bottle were shaken at 300 rpm for 6 hours at 5° C., then the bottle was vented, the cap removed, and the contents of the bottle transferred to a 1.5 mL microcentrifuge tube. The cells were briefly spun down, and a 100 μl aliquot of the supernatant analyzed by HPLC. The cell pellet was then assayed for recovered glycolate oxidase and catalase activity; recoveries of enzyme activities were based on the initial enzyme activities of the whole cells, and recoveries of greater than 100% are attributed to permeabilization of the cells over the course of the reaction.

| catalyst | time (h) | glyoxylate (%) | G.O. recovery (%) | Catalase recovery (%) |
|---|---|---|---|---|
| ST17SYG | 6 | 45 | 134 | 119 |
| ST17SYG/OL | 6 | 65 | 309 | 316 |
| ST17SYG/OL2 | 6 | 51 | 847 | 254 |
| ST17SYG/OLHA | 6 | 24 | 219 | 180 |
| ST17SYCSL/OL | 6 | 53 | 102 | 60 |
| FT17SYG/OL | 6 | 47 | 164 | 79 |
| ST17MIN | 6 | 25 | 66 | 346 |
| ST18MIN | 6 | 14 | 13 | 390 |
| ST17SYG/OL | 23 | 100 | 0 | 597 |
| ST17SYCSL/OL | 23 | 100 | 0 | 64 |
| FT17SYG/OL | 23 | 100 | 144 | 157 |

EXAMPLE 7

A 300-mL EZE-Seal stirred autoclave reactor (Autoclave Engineers) was charged with 75 mL of a solution containing glycolic acid (0.75M), ethylenediamine (0.86M, pH 9.2), propionic acid (0.075M, HPLC internal standard), and flavin mononucleotide (0.01 mM), and the solution cooled to 15° C. To the reactor was then added 14 g of frozen (−80° C.) *Aspergillus nidulans* ST17SYG/OL (25.2 IU glycolate oxidase and 20,400 IU catalase), and the cells were allowed to thaw at 15° C. The resulting mixture was stirred at 400 rpm and 15° C. under 70 psig (483 kPa) of oxygen, while bubbling oxygen through the mixture at 20 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 7 hours, the yields of glyoxylic acid, oxalic acid, and formic acid were 79%, 0%, and 0%, respectively, with 2.7% recovery of glycolic acid. The final activities of glycolate oxidase and catalase were 55% and 80% of their initial values.

EXAMPLE 8

A 300-mL EZE-Seal stirred autoclave reactor (Autoclave Engineers) was charged with 100 mL of a solution containing glycolic acid (0.75M), ethylenediamine (0.86M, pH 9.2), propionic acid (0.075M, HPLC internal standard), and flavin mononucleotide (0.01 mM), and the solution cooled to 5° C. To the reactor was then added 32 g of frozen (−80° C.) *Aspergillus nidulans* FT17SYG/OL (28.2 IU glycolate oxidase and 157,000 IU catalase), and the cells were allowed to thaw at 15° C. The resulting mixture was stirred at 400 rpm and 5° C. under 70 psig (483 kPa) of oxygen, while bubbling oxygen through the mixture at 30 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 21 hours, the yields of glyoxylic acid, oxalic acid, and formic acid were 88.2%, 0%, and 0%, respectively, with 10.0% recovery of glycolic acid. The final activities of glycolate oxidase and catalase were 0% and 75% of their initial values.

EXAMPLE 9

A 300-mL EZE-Seal stirred autoclave reactor (Autoclave Engineers) was charged with 100 mL of a solution containing glycolic acid (0.75M), ethylenediamine (0.86M, pH 9.0), propionic acid (0.075M, HPLC internal standard), and flavin mononucleotide (0.01 mM), and the solution cooled to 5° C. To the reactor was then added 26 g of frozen (−80° C.) *Aspergillus nidulans* FT17SYG/OL (29.9 IU glycolate oxidase and 177,000 IU catalase), and the cells were allowed to thaw at 5° C. The resulting mixture was stirred at 400 rpm and 5° C. under 70 psig (483 kPa) of oxygen, while bubbling oxygen through the mixture at 50 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 23 hours, the yields of glyoxylic acid, oxalic acid, and formic acid were 95%, 0%, and 0%, respectively, with complete conversion of glycolic acid. The final activities of glycolate oxidase and catalase were 12% and 76% of their initial values.

EXAMPLE 10

A 300-mL EZE-Seal stirred autoclave reactor (Autoclave Engineers) was charged with 100 mL of a solution containing glycolic acid (0.75M), ethylenediamine (0.86M, pH 9.0), propionic acid (0.075M, HPLC internal standard), and flavin mononucleotide (0.01 mM), and the solution cooled to 5° C. To the reactor was then added 26 g of frozen (−80° C.) *Aspergillus nidulans* FT17SYG/OL (24 IU glycolate oxidase and 192,000 IU catalase), and the cells were allowed to thaw at 5° C. The resulting mixture was stirred at 400 rpm and 5° C. under 120 psig of oxygen, while bubbling oxygen through the mixture at 50 mL/min. The reaction was monitored by taking a 100 μL aliquot of the reaction mixture at regular intervals, mixing the aliquot with 300 μL of 0.1N sulfuric acid to quench the reaction, filtering the aliquot and analyzing by HPLC. After 11.5 hours, the yields of glyoxylic acid, oxalic acid, and formic acid were 98%, 0%, and 0%, respectively, with complete conversion of glycolic acid. The final activities of glycolate oxidase and catalase were 100% and 62% of their initial values.

At the completion of the reaction, the reaction mixture was centrifuged at 5° C. and the supernatant decanted. The resulting pellet of *Aspergillus nidulans* cells was resuspended in 100 mL of fresh reaction mixture at 5° C., and the reaction repeated under conditions identical to those described above. After 16 hours, the yields of glyoxylic acid, oxalic acid, and formic acid were 47%, 0%, and 0%, respectively, with a 54% recovery of glycolic acid. The recovered activities of glycolate oxidase and catalase at 16 hours were 91% and 100% of their initial values.

EXAMPLE 11

Into a 3 oz. Fischer-Porter glass aerosol reaction vessel was placed a magnetic stirring bar and 10 mL of an aqueous solution containing glycolic acid (0.750M), ethylenediamine (0.863M), isobutyric acid (0.100M, HPLC internal standard), and flavin mononucleotide (0.01 mM) at pH 9.0, and the solution cooled to 5° C. To the vessel was then added 0.75 g of *Pichia pastoris* transformant strain GS115-MSP10 (31 IU glycolate oxidase and 38,100 IU catalase) which had been permeabilized by treatment with 0.1% "TRITON" X-100/1 freeze-thaw, and the reaction vessel sealed and the reaction mixture was cooled to 5° C. The vessel was flushed with oxygen by pressuring to 70 psig and venting to atmospheric pressure five times with stirring, then the vessel was pressurized to 70 psig of oxygen and the mixture stirred at 5° C. Aliquots (0.20 mL) were removed by syringe through a sampling port (without loss of pressure in the vessel) at regular intervals for analysis by HPLC to monitor the progress of the reaction. After 6 h, the HPLC yields of glyoxylate, formate, and oxalate were 98.2%, 0%, and 0% respectively, and no glycolate remained. The remaining permeabilized-cell glycolate oxidase and catalase activity were 85% and 117% respectively, of their initial values.

The microbial cell catalyst was recovered from the reaction mixture described above by centrifugation. Without further treatment the cell pellet was mixed with 10 mL of fresh reaction mixture, and the reaction repeated. This catalyst recycle procedure was performed for ten consecutive batch reactions, and the reaction time, the recovery of catalase and glycolate oxidase activity (based on the initial activity of the permeabilized cells), and yields of glyoxylic, formic, oxalic, and glycolic acid are listed in the table below:

| run # | time (h) | catalase (%) | glycolate oxidase (%) | glyoxylic acid(%) | formic acid(%) | oxalic acid(%) | glycolic acid(%) |
|---|---|---|---|---|---|---|---|
| 1 | 6.0 | 117 | 85 | 98.2 | 0 | 0 | 0 |
| 2 | 4.0 | 78 | 78 | 99.6 | 0 | 0 | 0 |
| 3 | 4.0 | 68 | 68 | 97.1 | 0 | 1.3 | 0 |
| 4 | 4.0 | 72 | 73 | 99.5 | 0 | 0.5 | 0 |
| 5 | 3.0 | 77 | 74 | 99.2 | 0 | 0.5 | 0 |
| 6 | 4.5 | 71 | 71 | 99.0 | 0 | 0.5 | 0 |
| 7 | 5.5 | 70 | 74 | 98.0 | 0 | 2.0 | 0 |
| 8 | 5.0 | 72 | 61 | 99.5 | 0 | 0.5 | 0 |
| 9 | 5.5 | 60 | 48 | 98.6 | 0 | 1.4 | 0 |
| 10 | 5.5 | 56 | 42 | 99.1 | 0 | 0.2 | 0 |

EXAMPLE 12

A 300-mL EZE-Seal stirred autoclave reactor equipped with Dispersimax Impeller (Autoclave Engineers) was charged with 100 mL of a solution containing glycolic acid (0.750M), ethylenediamine (0.863M), isobutyric acid (0.100M, HPLC internal standard), and flavin mononucleotide (0.01 mM), at pH 9.25, and the solution cooled to 5° C. To the reactor was then added 5.0 g of *Pichia pastoris* transformant strain GS115-MSP10 (423 IU glycolate oxidase and 869,000 IU catalase) which had been permeabilized by treatment with 0.1% benzalkonium chloride (Sigma), and the reactor purged with oxygen. The mixture was then stirred at 1000 rpm, which bubbled oxygen through the mixture via the action of the turbine impeller, and at 5° C. under 120 psig of oxygen. The reaction was monitored by taking a 0.4 mL aliquot of the reaction mixture at regular intervals, filtering the aliquot using a Millipore Ultrafree-MC 10,000 NMWL Filter Unit, and analyzing the filtrate by HPLC. After 1.0 h, the yields of glyoxylic acid, oxalic acid, and formic acid were 98.7%, 1.3%, and 0%, respectively, with no remaining glycolic acid. The recovered activities of permeabilized-cell glycolate oxidase and catalase were 87% and 84% of their initial values, respectively.

The microbial cell catalyst was recovered from the reaction mixture described above by centrifugation. Without further treatment the cell pellet was mixed with 100 mL of fresh reaction mixture, and the reaction repeated. This catalyst recycle procedure was performed for twenty consecutive batch reactions, and the reaction time, the recovery of catalase and glycolate oxidase activity (based on the initial activity of the permeabilized cells), and yields of glyoxylic, formic, oxalic, and glycolic acid are listed in the table below:

| run # | time (h) | catalase (%) | glycolate oxidase (%) | glyoxylic acid(%) | formic acid(%) | oxalic acid(%) | glycolic acid(%) |
|---|---|---|---|---|---|---|---|
| 1 | 1.0 | 84 | 87 | 98.7 | 0 | 1.3 | 0 |
| 2 | 1.0 | 88 | 104 | 98.7 | 0 | 1.3 | 0 |
| 3 | 1.0 | 85 | 107 | 98.8 | 0 | 1.2 | 0 |
| 4 | 1.0 | 79 | 126 | 98.7 | 0 | 1.3 | 0 |
| 5 | 1.0 | 69 | 104 | 98.8 | 0 | 1.2 | 0 |
| 6 | 1.0 | 79 | 109 | 98.9 | 0 | 1.1 | 0 |
| 7 | 1.0 | 71 | 110 | 99.3 | 0 | 0.7 | 0 |
| 8 | 1.0 | 64 | 113 | 99.2 | 0 | 0.8 | 0 |
| 9 | 1.0 | 61 | 106 | 99.4 | 0 | 0.6 | 0 |
| 10 | 1.0 | 61 | 101 | 99.1 | 0 | 0.9 | 0 |
| 11 | 1.0 | 72 | 104 | 99.5 | 0 | 0.5 | 0 |
| 12 | 1.0 | 68 | 99 | 99.4 | 0 | 0.6 | 0 |
| 13 | 1.5 | 70 | 101 | 99.3 | 0 | 0.7 | 0 |
| 14 | 1.5 | 59 | 96 | 99.6 | 0 | 0.4 | 0 |
| 15 | 1.5 | 58 | 86 | 99.6 | 0 | 0.4 | 0 |
| 16 | 1.75 | 58 | 83 | 99.6 | 0 | 0.4 | 0 |
| 17 | 2.0 | 56 | 77 | 97.2 | 0 | 2.8 | 0 |
| 18 | 2.0 | 37 | 91 | 99.7 | 0 | 0.3 | 0 |
| 19 | 2.5 | 50 | 73 | 99.7 | 0 | 0.3 | 0 |
| 20 | 3.5 | 46 | 72 | 99.9 | 0 | 0.1 | 0 |

| run # | time (h) | catalase (%) | glycolate oxidase (%) | glyoxylic acid(%) | formic acid(%) | oxalic acid(%) | glycolic acid(%) |
|---|---|---|---|---|---|---|---|
| 1 | 0.75 | 105 | 104 | 99.1 | 0 | 0.3 | 0.6 |
| 2 | 1.0 | 85 | 101 | 99.7 | 0 | 0.3 | 0 |
| 3 | 1.5 | 82 | 97 | 99.6 | 0 | 0.4 | 0 |
| 4 | 1.5 | 67 | 96 | 99.8 | 0 | 0.2 | 0 |
| 5 | 2.0 | 92 | 93 | 99.7 | 0 | 0.3 | 0 |

EXAMPLE 13

A 300-mL EZE-Seal stirred autoclave reactor equipped with Dispersimax Impeller (Autoclave Engineers) was charged with 100 mL of a solution containing glycolic acid (0.750M), ethylenediamine (0.863M), isobutyric acid (0.100M, HPLC internal standard), and flavin mononucleotide (0.01 mM), at pH 9.25, and the solution cooled to 5° C. To the reactor was then added 2.0 g of *Pichia pastoris* transformant strain GS115-MSP10 (2763 IU glycolate oxidase and 494,000 IU catalase) which had been permeabilized by treatment with 0.1% Triton X-100/6 freeze-thaws, and the reactor purged with oxygen. The mixture was then stirred at 1000 rpm, which bubbled oxygen through the mixture via the action of the turbine impeller, and at 5° C. under 120 psig of oxygen. The reaction was monitored by taking a 0.4 mL aliquot of the reaction mixture at regular intervals, filtering the aliquot using a Millipore Ultrafree-MC 10,000 NMWL Filter Unit, and analyzing the filtrate by HPLC. After 0.75 h, the yields of glyoxylic acid, oxalic acid, and formic acid were 99.1%, 0.3%, and 0%, respectively, with 0.6% glycolic acid remaining. The recovered activities of permeabilized-cell glycolate oxidase and catalase were 104% and 105% of their initial values, respectively.

The microbial cell catalyst was recovered from the reaction mixture described above by centrifugation. Without further treatment the cell pellet was mixed with 100 mL of fresh reaction mixture, and the reaction repeated. After 1.0 h, the yields of glyoxylic acid, oxalic acid, and formic acid were 99.7%, 0.3%, and 0%, respectively, with no glycolic acid remaining. The recovered activities of permeabilized-cell glycolate oxidase and catalase were 101% and 85% of their initial values. This catalyst recycle procedure was performed for five consecutive batch reactions, and the reaction time, the recovery of catalase and glycolate oxidase activity (based on the initial activity of the permeabilized cells), and yields of glyoxylic, formic, oxalic, and glycolic acid are listed in the table below:

EXAMPLE 14

A 300-mL EZE-Seal stirred autoclave reactor equipped with Dispersimax Impeller (Autoclave Engineers) was charged with 100 mL of a solution containing glycolic acid (1.500M), ethylenediamine (1.575M), isobutyric acid (0.300M, HPLC internal standard), and flavin mononucleotide (0.01 mM), at pH 9.25, and the solution cooled to 5° C. To the reactor was then added 2.0 g of *Pichia pastoris* transformant strain GS115-MSP10 (114 IU glycolate oxidase and 148,000 IU catalase) which had been permeabilized by treatment with 0.1% Triton X-100/1 freeze-thaw, and the reactor purged with oxygen. The mixture was then stirred at 1000 rpm, which bubbled oxygen through the mixture via the action of the turbine impeller, and at 5° C. under 120 psig of oxygen. The reaction was monitored by taking a 0.4 mL aliquot of the reaction mixture at regular intervals, filtering the aliquot using a Millipore Ultrafree-MC 10,000 NMWL Filter Unit, and analyzing the filtrate by HPLC. After 4.5 h, the yields of glyoxylic acid, oxalic acid, and formic acid were 98.0%, 0.4%, and 0%, respectively, with no glycolic acid remaining. The final activities of permeabilized-cell glycolate oxidase and catalase were 136% and 113% of their initial values, respectively.

EXAMPLE 15

Into a 3 oz. Fischer-Porter glass aerosol reaction vessel was placed a magnetic stirring bar and 10 mL of an aqueous solution containing glycolic acid (0.750M), ethylenediamine (0.863M), isobutyric acid (0.100M, HPLC internal standard), and flavin mononucleotide (0.01 mM) at pH 9.0, and the solution cooled to 5° C. To the vessel was then added 0.475 g of *Hansenula polymorpha* transformant GO1 (10.0 IU glycolate oxidase and 22,100 IU catalase) which had been permeabilized by treatment with 0.1% "TRITON" X-100/1 freeze-thaw, and the reaction vessel sealed and the reaction mixture was cooled to 5° C. The vessel was flushed with oxygen by pressuring to 70 psig and venting to atmospheric pressure five times with stirring, then the vessel was pressurized to 70 psig of oxygen and the mixture stirred at 5° C. Aliquots (0.20 mL) were removed by syringe through a sampling port (without loss of pressure in the vessel) at regular intervals for analysis by HPLC to monitor the progress of the reaction. After 16 h, the HPLC yields of glyoxylate, formate, and oxalate were 97.1%, 2.9%, and 0% respectively, and no glycolate remained. The remaining permeabilized-cell glycolate oxidase and catalase activity were 107% and 231% respectively, of their initial values.

EXAMPLE 16

A 300-mL EZE-Seal stirred autoclave reactor equipped with Dispersimax Impeller (Autoclave Engineers) was charged with 100 mL of a solution containing glycolic acid (0.750M), ethylenediamine (0.863M), isobutyric acid (0.100M, HPLC internal standard), and flavin mononucleotide (0.01 mM), at pH 9.3, and the solution cooled to 5° C. To the reactor was then added 11.9 g of *Hansenula polymorpha* transformant strain GO1 (100 IU glycolate oxidase and 998,000 IU catalase) which had been permeabilized by treatment with 0.1% Triton X-100/1 freeze-thaw, and the reactor purged with oxygen. The mixture was then stirred at 500 rpm, and oxygen was bubbled through the mixture at 100 mL/min using a sparge tube located below the surface of the reaction mixture. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC. After 2.25 h, the yields of glyoxylic acid, oxalic acid, and formic acid were 100%, 0%, and 0%, respectively, with no glycolic acid remaining. The recovered activities of permeabilized-cell glycolate oxidase and catalase were 158% and 82% of their initial values, respectively.

EXAMPLE 17

The reaction in Example 16 was repeated using 15.0 g of *Hansenula polymorpha* transformant GO1 (109 IU glycolate oxidase and 530,000 IU catalase) which had been permeabilized by treatment with 0.1% Triton X-100/1 freeze-thaw. The mixture was then stirred at 500 rpm and at 5° C. under 120 psig of oxygen, and oxygen was bubbled through the mixture at 50 mL/min using a sparge tube located below the surface of the reaction mixture. After 3.75 h, the yields of glyoxylic acid, oxalic acid, and formic acid were 100%, 0%, and 0%, respectively, with no glycolic acid remaining. The recovered activities of permeabilized-cell glycolate oxidase and catalase were 85% and 166% of their initial values, respectively.

EXAMPLE 18

The reaction in Example 16 was repeated using 15.0 g of *Hansenula polymorpha* transformant GO1 (51 IU glycolate oxidase and 730,000 IU catalase) which had been permeabilized by treatment with 0.1% Triton X-100/1 freeze-thaw. The mixture was stirred at 1250 rpm, which bubbled oxygen through the mixture via the action of the Dispersimax turbine impeller, and at 5° C. under 120 psig of oxygen. After 4.0 h, the yields of glyoxylic acid, oxalic acid, and formic acid were 97.5%, 0%, and 0%, respectively, with 0.6% glycolic acid remaining. The recovered activities of permeabilized-cell glycolate oxidase and catalase were 132% and 129% of their initial values, respectively.

EXAMPLE 19

A 300-mL EZE-Seal stirred autoclave reactor equipped with Dispersimax Impeller (Autoclave Engineers) was charged with 100 mL of a solution containing glycolic acid (0.750M), ethylenediamine (0.863M), isobutyric acid (0.100M, HPLC internal standard), and flavin mononucleotide (0.01 mM), at pH 9.3, and the solution cooled to 5° C. To the reactor was then added 15.0 g of *Hansenula polymorpha* transformant strain GO1 (262 IU glycolate oxidase and $1.135 \times 10^6$ IU catalase) which had been permeabilized by treatment with 0.1% Triton X-100/1 freeze-thaw, and the reactor purged with oxygen. The mixture was then stirred at 1000 rpm, which bubbled oxygen through the mixture via the action of the turbine impeller, and at 5° C. under 250 psig of oxygen. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC. After 1.0 h, the yields of glyoxylic acid, oxalic acid, and formic acid were 96.9%, 0.3%, and 0%, respectively, with no remaining glycolic acid. The recovered activities of permeabilized-cell glycolate oxidase and catalase were 98% and 124% of their initial values, respectively.

The microbial cell catalyst was recovered from the reaction mixture described above by centrifugation. Without further treatment the cell pellet was mixed with 100 mL of fresh reaction mixture, and the reaction repeated. This catalyst recycle procedure was performed for eight consecutive batch reactions, and the reaction time, the recovery of catalase and glycolate oxidase activity (based on the initial activity of the permeabilized cells), and yields of glyoxylic, formic, oxalic, and glycolic acid are listed in the table below:

| run # | time (h) | catalase (%) | glycolate oxidase (%) | glyoxylic acid(%) | formic acid(%) | oxalic acid(%) | glycolic acid(%) |
|---|---|---|---|---|---|---|---|
| 1 | 1.0 | 124 | 98 | 96.9 | 0 | 0.3 | 0.6 |
| 2 | 1.5 | 145 | 84 | 99.6 | 0 | 0.4 | 0 |
| 3 | 2.0 | 162 | 77 | 97.4 | 0 | 0.3 | 0 |
| 4 | 2.0 | 117 | 57 | 94.6 | 0 | 1.0 | 0 |
| 5 | 2.5 | 128 | 44 | 97.7 | 0 | 0.7 | 0 |
| 6 | 3.0 | 133 | 40 | 96.6 | 0 | 0.1 | 0 |
| 7 | 5.0 | 111 | 23 | 99.1 | 0 | 0.2 | 0 |
| 8 | 16.5 | 116 | 19 | 95.2 | 0 | 0.3 | 0 |

EXAMPLE 20

The reaction in Example 19 was repeated except that FMN was not added to the reaction mixture. The catalyst was 5.0 g of *Hansenula polymorpha* transformant GO1 (880 IU glycolate oxidase and 453,000 IU catalase) which had been permeabilized by treatment with 0.1% Triton X-100/1 freeze-thaw. The catalyst recycle procedure was performed for twenty consecutive batch reactions with no added FMN, and the reaction time, the recovery of catalase and glycolate oxidase activity (based on the initial activity of the permeabilized cells), and yields of glyoxylic, formic, oxalic, and glycolic acid are listed in the table below:

| run # | time (h) | catalase (%) | glycolate oxidase (%) | glyoxylic acid(%) | formic acid(%) | oxalic acid(%) | glycolic acid(%) |
|---|---|---|---|---|---|---|---|
| 1 | 1.0 | 100 | 100 | 96.9 | 0.1 | 1.1 | 1.2 |
| 2 | 1.0 | 88 | 109 | 98.4 | 0.1 | 1.2 | 1.4 |
| 3 | 1.0 | 102 | 110 | 98.2 | 0.1 | 1.0 | 0.9 |
| 4 | 1.0 | 103 | 107 | 98.0 | 0.1 | 1.0 | 0.9 |
| 5 | 1.0 | 86 | 90 | 97.8 | 0.2 | 1.1 | 1.1 |
| 6 | 1.0 | 85 | 95 | 98.4 | 0.1 | 0.9 | 1.1 |
| 7 | 1.0 | 89 | 116 | 97.9 | 0.1 | 0.9 | 1.1 |
| 8 | 1.3 | 89 | 116 | 99.1 | 0.1 | 1.1 | 1.0 |
| 9 | 1.0 | 87 | 103 | 98.0 | 0.1 | 1.0 | 1.0 |
| 10 | 1.0 | 106 | 116 | 98.3 | 0.1 | 0.8 | 0.8 |
| 11 | 1.0 | 85 | 104 | 97.9 | 0.1 | 0.8 | 0.9 |
| 12 | 1.5 | 99 | 101 | 96.6 | 0.1 | 0.8 | 1.0 |
| 13 | 1.5 | 98 | 105 | 98.1 | 0.1 | 0.7 | 1.0 |
| 14 | 1.0 | 78 | 85 | 98.5 | 0.1 | 0.6 | 1.8 |
| 15 | 1.0 | 88 | 82 | 98.3 | 0.2 | 0.5 | 1.1 |
| 16 | 1.0 | 90 | 82 | 99.6 | 0.1 | 0.5 | 0.8 |
| 17 | 1.0 | 59 | 56 | 98.8 | 0 | 0.5 | 1.0 |
| 18 | 1.0 | 48 | 60 | 97.7 | 0.6 | 0.4 | 1.5 |
| 19 | 1.0 | 54 | 63 | 98.6 | 0.1 | 0.6 | 1.7 |
| 20 | 1.5 | 86 | 61 | 98.0 | 0.1 | 0.7 | 1.3 |

EXAMPLE 21

A 300-mL EZE-Seal stirred autoclave reactor equipped with Dispersimax Impeller (Autoclave Engineers) was charged with 100 mL of a solution containing glycolic acid (0.750M), ethylenediamine (0.863M), isobutyric acid (0.100M, HPLC internal standard), and flavin mononucleotide (0.01 mM), at pH 9.2, and the solution cooled to 5° C. To the reactor was then added 30 g of *E. coli* transformant d01 (72 IU glycolate oxidase and 29,600 IU catalase), and the mixture stirred at 1000 rpm, which bubbled oxygen through the mixture via the action of the turbine impeller, and at 5° C. under 120 psig of oxygen. The reaction was monitored by taking a 0.40 mL aliquot of the reaction mixture at regular intervals, filtering the aliquot using a Millipore Ultrafree-MC 10,000 NMWL Filter Unit, and analyzing the filtrate by HPLC. After 23 h, the yields of glyoxylic acid, oxalic acid, and formic acid were 74.4%, 1.1%, and 5.6%, respectively, with 6.3% glycolic acid remaining. The recovered activities of microbial glycolate oxidase and catalase were 30% and 199% of their initial values, respectively.

Having thus described and exemplified the invention with a certain degree of particularity, it should be appreciated that the following claims are not to be so limited but are to be afforded a scope commensurate with the wording of each element of the claim and equivalents thereof.

What is claimed is:

1. In a process for preparing glyoxylic acid comprising the step of oxidizing glycolic acid with oxygen in aqueous solution of glycolic acid, an amine and the enzymes glycolate oxidase and catalase, the improvement comprising:

(a) using the enzyme glycolate oxidase in the form of a microbial cell transformant that intracellularly expresses and retains in the cytoplasm or peroxisomes glycolate oxidase selected from the group consisting of transformants of *Aspergillus nidulans, Hansenula polymorpha, Pichia pastoris,* and *Escherichia coli*, under conditions where the transformants are permeabilized to the passage of carboxylic acids, (b) sparging oxygen into the resulting aqueous mixture, and (c) selecting the amine from the group consisting of ethylenediamine, tris(hydroxymethyl)aminomethane, piperazine, glycylglycine, and mixtures thereof.

2. The process of claim 1 wherein said microbial cell transformant also expresses endogenous catalase.

3. The process of claim 1, further comprising adding soluble catalase to the mixture.

4. The process of claim 1 wherein said microbial cell transformant is *Aspergillus nidulans* T17 designated NRRL 21000.

5. The process of claim 1 wherein said microbial cell transformant is *Pichia pastoris* GS115-MSP10 designated NRRL Y-21001.

6. The process of claim 1 wherein said microbial cell transformant is *Pichia pastoris* MSP12 designated NRRL Y-21040.

7. The process of claim 1 wherein said microbial cell transformant is *Hansenula polymorpha* GO1 designated NRRL Y-21065.

8. The process of claim 1 wherein the amine is ethylenediamine.

9. The process of claim 1 wherein the amine is tris(hydroxymethyl)aminomethane.

10. The process of claim 1 wherein the amine is piperazine.

11. The process of claim 1 wherein the amine is glycylglycine.

\* \* \* \* \*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 369 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:1:

```
Met Glu Ile Thr Asn Val Asn Glu Tyr Glu Ala Ile Ala Lys Gln Lys
  1               5                  10                  15
Leu Pro Lys Met Val Tyr Asp Tyr Tyr Ala Ser Gly Ala Glu Asp Gln
             20                  25                  30
Trp Thr Leu Ala Glu Asn Arg Asn Ala Phe Ser Arg Ile Leu Phe Arg
         35                  40                  45
Pro Arg Ile Leu Ile Asp Val Thr Asn Ile Asp Met Thr Thr Thr Ile
     50                  55                  60
Leu Gly Phe Lys Ile Ser Met Pro Ile Met Ile Ala Pro Thr Ala Met
 65                  70                  75                  80
Gln Lys Met Ala His Pro Glu Gly Glu Tyr Ala Thr Ala Arg Ala Ala
                 85                  90                  95
Ser Ala Ala Gly Thr Ile Met Thr Leu Ser Ser Trp Ala Thr Ser Ser
            100                 105                 110
Val Glu Glu Val Ala Ser Thr Gly Pro Gly Ile Arg Phe Phe Gln Leu
        115                 120                 125
Tyr Val Tyr Lys Asp Arg Asn Val Val Ala Gln Leu Val Arg Arg Ala
    130                 135                 140
Glu Arg Ala Gly Phe Lys Ala Ile Ala Leu Thr Val Asp Thr Pro Arg
145                 150                 155                 160
Leu Gly Arg Arg Glu Ala Asp Ile Lys Asn Arg Phe Val Leu Pro Pro
                165                 170                 175
Phe Leu Thr Leu Lys Asn Phe Glu Gly Ile Asp Leu Gly Lys Met Asp
            180                 185                 190
Lys Ala Asn Asp Ser Gly Leu Ser Ser Tyr Val Ala Gly Gln Ile Asp
        195                 200                 205
Arg Ser Leu Ser Trp Lys Asp Val Ala Trp Leu Gln Thr Ile Thr Ser
    210                 215                 220
Leu Pro Ile Leu Val Lys Gly Val Ile Thr Ala Glu Asp Ala Arg Leu
225                 230                 235                 240
```

-continued

| Ala | Val | Gln | His | Gly<br>245 | Ala | Ala | Gly | Ile | Ile<br>250 | Val | Ser | Asn | His | Gly<br>255 | Ala |
|---|---|---|---|---|---|---|---|---|---|---|---|---|---|---|---|
| Arg | Gln | Leu | Asp<br>260 | Tyr | Val | Pro | Ala | Thr<br>265 | Ile | Met | Ala | Leu | Glu<br>270 | Glu | Val |
| Val | Lys | Ala<br>275 | Ala | Gln | Gly | Arg | Ile<br>280 | Pro | Val | Phe | Leu | Asp<br>285 | Gly | Gly | Val |
| Arg | Arg<br>290 | Gly | Thr | Asp | Val | Phe<br>295 | Lys | Ala | Leu | Ala | Leu<br>300 | Gly | Ala | Ala | Gly |
| Val<br>305 | Phe | Ile | Gly | Arg | Pro<br>310 | Val | Val | Phe | Ser | Leu<br>315 | Ala | Ala | Glu | Gly | Glu<br>320 |
| Ala | Gly | Val | Lys | Lys<br>325 | Val | Leu | Gln | Met | Met<br>330 | Arg | Asp | Glu | Phe | Glu<br>335 | Leu |
| Thr | Met | Ala | Leu<br>340 | Ser | Gly | Cys | Arg | Ser<br>345 | Leu | Lys | Glu | Ile | Ser<br>350 | Arg | Ser |
| His | Ile | Ala<br>355 | Ala | Asp | Trp | Asp | Gly<br>360 | Pro | Ser | Ser | Arg | Ala<br>365 | Val | Ala | Arg |

Leu ( 2 ) INFORMATION FOR SEQ ID NO:2:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TACCGAATTC ATGGAGATCA CAAATGTG        28

( 2 ) INFORMATION FOR SEQ ID NO:3:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

AACAGAATTC TTATAATCTG GCAACAGA        28